United States Patent [19]

Labrie et al.

[11] Patent Number: 5,204,337
[45] Date of Patent: Apr. 20, 1993

[54] ESTROGEN NUCLEUS DERIVATIVES FOR USE IN INHIBITION OF SEX STEROID ACTIVITY

[75] Inventors: Fernand Labrie; Yves Mérand, both of Ste-Foy, Canada

[73] Assignee: Endorecherche Inc., Canada

[21] Appl. No.: 917,915

[22] Filed: Jul. 21, 1992

Related U.S. Application Data

[63] Continuation of Ser. No. 377,010, Jul. 7, 1989, abandoned, which is a continuation-in-part of Ser. No. 322,154, Mar. 10, 1989, which is a continuation-in-part of Ser. No. 265,716, Nov. 1, 1988, abandoned, which is a continuation-in-part of Ser. No. 265,150, Oct. 31, 1988, abandoned.

[51] Int. Cl.⁵ .................... C07J 41/00; A61K 31/56
[52] U.S. Cl. ........................... 514/182; 540/83; 548/494; 564/171; 564/172; 552/510; 552/528; 552/536; 552/538; 552/540; 552/626
[58] Field of Search ............... 514/186; 552/536, 538, 552/540, 626

[56] References Cited

U.S. PATENT DOCUMENTS

| | | | |
|---|---|---|---|
| 2,875,199 | 2/1959 | Cella et al. | 540/41 |
| 3,493,606 | 2/1970 | Richardson | 564/356 |
| 3,562,260 | 2/1971 | Ruggieri et al. | 552/626 |
| 3,637,856 | 1/1972 | Richardson | 564/323 |
| 4,096,253 | 6/1978 | Wachter et al. | 552/536 |

(List continued on next page.)

FOREIGN PATENT DOCUMENTS

| | | |
|---|---|---|
| 8541657 | 4/1985 | Australia . |
| 2097 | 5/1979 | European Pat. Off. . |
| 0011372 | 5/1980 | European Pat. Off. . |
| 11372 | 5/1980 | European Pat. Off. . |
| 19377 | 11/1980 | European Pat. Off. . |

(List continued on next page.)

OTHER PUBLICATIONS

Wakeling et al. (I), CA 106:149712y (1987).
Wakeling et al. (II), CA 109:104945x (1988).

Levesque et al., *J. Med. Chem.* 34, (1991), pp. 1624–1630.

(List continued on next page.)

*Primary Examiner*—Mukund J. Shah
*Assistant Examiner*—Philip I. Datlow
*Attorney, Agent, or Firm*—Ostrolenk, Faber, Gerb & Soffen

[57] ABSTRACT

Novel compounds for the inhibition of sex steroid activity for the treatment of both androgen-related and estrogen-related diseases include for example 15- and 16-halo substituted compounds such as:

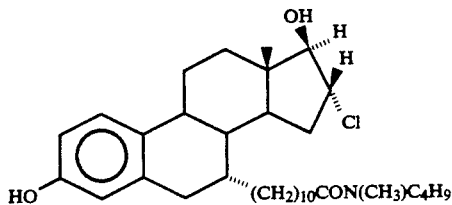

The compounds are characterized by an estrogenic nucleus substituted with a substituent of the formula $-R^1[B-R^2-]_xL-G$ wherein
at least one of L and G is a polar moiety distanced from a ring carbon of the estrogenic nucleus by a least three intervening atoms:
x is an integer from 0–6;
$R^1$ and $R^2$ are independently either absent or selected from the group consisting of straight- or branched-chain alkylene, straight- or branched-chain alkynylene, straight- or branched-chain alkenylene, phenylene, and fluoro-substituted analogs of the foregoing; and
B is either absent or selected from the group consisting of $-O-$, $-Se-$, $-SO-$, $-SO_2-$, $-NR^3-$, $-SiR^3{}_2$, $-CR^3OR^3-$, $NR^3CO-$, $NR^3CS-$, $-CONR^3-$, $CSNR^3-$, $-COO-$, $-COS-$, $-S-CO-$, $-CSS-$, $-SCS-$, $-OCO-$ and phenylene ($R^3$ being hydrogen or lower alkyl).

10 Claims, 2 Drawing Sheets

U.S. PATENT DOCUMENTS

| | | |
|---|---|---|
| 4,198,435 | 4/1980 | Richardson .......................... 424/330 |
| 4,307,111 | 12/1981 | Crawley ................................ 428/278 |
| 4,472,382 | 9/1984 | Labrie et al. .......................... 514/15 |
| 4,536,516 | 8/1985 | Harper et al. ........................ 514/514 |
| 4,623,660 | 11/1986 | Richardson .......................... 514/514 |
| 4,659,516 | 4/1987 | Bowler et al. ........................ 552/628 |
| 4,659,695 | 4/1987 | Labrie ................................... 514/15 |
| 4,728,640 | 3/1988 | Labrie et al. .......................... 514/15 |
| 4,732,912 | 3/1988 | Pilgrim et al. ........................ 514/510 |
| 4,743,589 | 5/1988 | Labrie et al. .......................... 514/15 |
| 4,745,102 | 5/1988 | Labrie et al. .......................... 514/15 |
| 4,751,240 | 6/1988 | Bowler et al. ........................ 514/510 |
| 4,760,053 | 7/1988 | Labrie ................................... 514/15 |
| 4,760,061 | 7/1988 | Edwards et al. ..................... 514/211 |
| 4,775,660 | 10/1988 | Labrie et al. .......................... 514/15 |

FOREIGN PATENT DOCUMENTS

| | | |
|---|---|---|
| 100172 | 2/1984 | European Pat. Off. . |
| 0124369 | 11/1984 | European Pat. Off. . |
| 138504 | 4/1985 | European Pat. Off. . |
| 160508 | 11/1985 | European Pat. Off. . |
| 163416 | 12/1985 | European Pat. Off. . |
| 124369 | 6/1987 | European Pat. Off. . |
| 3242894 | 5/1984 | Fed. Rep. of Germany . |
| 0280618 | 8/1988 | France . |
| 0305242 | 3/1989 | France . |
| 8501454 | 2/1986 | PCT Int'l Appl. . |
| 0138504 | 4/1985 | United Kingdom . |

OTHER PUBLICATIONS

Heiman et al., *J. Med. Chem.*, 23, (1980), pp. 994–1002.

Fevig et al., *Steroids*, 51, (1988), pp. 471–497.

Landvatter et al., "Non Steroidal Estrogens: Synthesis and Estrogen Receptor Binding Affinity of Derivatives", *J. Med. Chem.* (1982).

Weatherill et al., "Interaction of the Antiestrogen ICI 164,384 with Oestrogen Receptor", *J. Steroid Biochem.*, vol. 30, No. 1–6, pp. 263–266 (1988).

Wakeling et al., "Steroidal Pure Antiestrogens", J. Endocr., 112, R7–R10 (1987).

Wakeling et al., Biology and Mode of Action of Pure Antioestrogen, *J. Steroid Biochem.* vol. 30, No. 1–6, pp. 141–147 (1988).

Doberauer et al., "Advanced Male Breast Cancer Treatment with the LH–RH Analog Buserlin Alone or in Combination with the Antiandrogen Flutamide", *Cancer* 62: pp. 474–478.

R. T. Blickenstaff, et al.: "Synthesis of Some Analogs of Estradiol", Steroids, vol. 46, No. 4,5, Nov. (1985), pp. 889–902.

ESTROGEN NUCLEUS DERIVATIVES FOR USE IN INHIBITION OF SEX STEROID ACTIVITY

RELATED APPLICATIONS

This is a continuation of application Ser. No. 07/377,010, filed on Jul. 7, 1989, now abandoned, which is a continuation-in-part of U.S. patent application Ser. No. 07/322,154 filed Mar. 10, 1989, still pending, which is a continuation-in-part of U.S. application Ser. No. 07/265,716 filed Nov. 1, 1988, now abandoned, which is a continuation-in-part of U.S. application Ser. No. 07/265,150 filed Oct. 31, 1988, now abandoned, the disclosures of which are incorporated herein by reference. (Ser. No. 07/265,716 has been refiled as U.S. Ser. No. 07/819,586, filed Jan. 9, 1992; Ser. No. 07/265,150 has been refiled as Ser. No. 07/913,746, filed Jul. 14, 1992).

BACKGROUND OF THE INVENTION

This invention relates to novel inhibitors of sex steroid activity such as antiestrogen compounds having effective antagonistic capability while substantially lacking agonistic effects. More particularly, certain preferred embodiments of the invention relate to certain estradiol and non-steroidal diphenylethylene analogs which have high affinity for estrogen receptors but do not activate such receptors and/or which inhibit the production of sex steroids or their precursors.

During the treatment of certain sex steroid-dependent diseases, it is important to greatly reduce or, if possible, eliminate certain sex steroid-induced effects. For this purpose, it is desirable both to block receptor sites stimulated by; sex steroids and also to reduce the amount of sex steroid available to act at these sites. For example, alternative or concurrent therapy to administration of antiestrogens could involve attempts to block the production of estrogens (e.g. by ovariectomy) such that less is available to activate receptor sites. However, prior art methods for blocking estrogen production insufficiently inhibit estrogen-induced functions. Moreover, it is possible that even in the total absence of sex steroids, unoccupied sex steroid receptors may be biologically active. Hence, antagonists of sex steroids may produce greater therapeutic results than therapy which only inhibits sex steroid production. Prior art antagonists, however, often have insufficient affinity for receptors, and some, although capable of binding the receptors, may themselves act as agonists and undesirably activate some receptors and induce the same effects as a sex steroid.

There is, therefore, a need in the art for antiestrogens which effectively block estrogen receptors with minimal or no agonistic effect. Numerous compounds have been tried in the art with mixed results. Known antiestrogens continue to exhibit undesirable agonistic activity. See, for instance, Wakeling and Bowler, "Steroidal Pure Antioestrogens", *J. Endocrinol.* (1987) 112, R7–R10. The net effectiveness of prior art compounds is determined by the balance between their agonistic and antagonistic activities. Certain steroidal derivatives similar to those disclosed in the foregoing article, and which are stated to have antioestrogenic effect, are set forth in Bowler et al., U.S. Pat. No. 4,659,516.

In U.S. Pat. No. 4,094,994, it is disclosed that the use of certain antiestrogens may inhibit certain human breast tumor cells.

H. Mooridsen et al., Cancer Treatment Review 5, 131–141, (1978), discloses that Tamoxiphen, an antiestrogen, is effective in remission of advanced breast cancer in about 30 percent of the women patients treated.

The combined used of the antiestrogen Tamoxiphen and a luteinizing hormone-releasing hormone agonist, Buserelin, is also known for treatment of breast cancer. See, for instance, Klijn et al., *J. Steroid Biochem*, 420, No. 6b, 1381 (1984). The objective remission of such cancers, however, remains unacceptable low.

It has been found that certain 7α-substituted derivatives of estradiol possess antiestrogenic activity (Bowler et al., 1985; Eur. Patent Application 0138504; Wakeling and Bowler, J. Steroid Biochem. 30: 141–147, 1988).

In U.S. Pat. No. 4,659,516, Bowler et al. report antiestrogenic activity for certain 7α substituted derivatives of estradiol.

For a number of years, there has been research for compounds which can efficiently inhibit androgen and-/or estrogen formation (e.g. enzyme inhibitors) or for compounds which may suppress androgen or estrogen action (steroid antagonists), without causing adverse effects to healthy tissues.

Recently, estradiol derivatives bearing a carboxyalkyl substituent at the 7α-position maintained their affinity for the estrogen receptor when linked via their carboxy group to agarose or polyacrylamide resin for affinity chromatography purification of the estrogen receptor (Bucourt et al., J. Biol. Chem. 253: 8221, 1978).

Non steroidal compounds bearing a similar aliphatic side chain have also been found to possess antiestrogenic activity (U.S. Pat. No. 4,732,912).

Some steroid derivatives, such as especially 16-methylene estradiol and 16-methylene estrone, have been described as inhibitors of 17β-hydroxysteroid dehydrogenase activity (Thomas et al., J. Biol. Chem. 258: 11500, 1983).

Prior art methods have not been completely effective in inhibiting sex steroid synthesis while avoiding undesirable side effects.

Certain nonsteroidal compounds which are stated to have antiandrogenic effect are described by Furr et al., J. Endocr. 113, R7–R9, 1987.

In U.S. Pat. No. 4,659,695 relates to a method of treatment of prostate cancer for susceptible male animals including humans whose testicular hormonal secretions are blocked by surgical or chemical means, e.g., by use of an LHRH agonist, e.g., [D-Trp[6], des-Gly-NH$_2$[10]]LHRH ethylamide. The treatment includes administering an antiandrogen, e.g., flutamide in association with at least one inhibitor of sex steroid biosynthesis, e.g., aminoglutethimide and/or ketoconazole.

U.S. Pat. No. 4,472,382 relates to a method of treating prostate cancer using the combination of an antiandrogen and an LHRH agonist.

In U.S. Pat. No. 4,386,080 relates to new amide derivatives, and more particularly novel acylanilides, possess antiandrogenic properties.

In French, Patent 2528434 and in Jordan and Koch, "Regulation of Prolactin Synthesis in vitro by estrogenic and antiestrogenic derivatives of estradiol and Estrone", Endocrinology 124(4): 1717–1725 (1989), antiestrogenic effects are described for certain 11β-long chain substituted estradiol derivatives.

In U.S. Pat. Nos. 3,995,060, 4,161,540 and 4,139,638, it is disclosed that certain 4'-substituted and 3'-, 4'-disubstituted anilides have antiandrogenic properties.

EP Pat. No. 138 504, EP Pat. No. 166 509, EP Pat. No. 124 369, EP Pat. No. 160 508, EP Pat. No. 163 416, U.S. Pat. Nos. 4,732,912, 4,760,061, 4,751,240, 4,659,516 and Wakeling A. E. and Bowler J., *J. Endocr.* 112, R7-R10, 1987, and *J. Steroid Biochem.* 30, 141-147, 1988 disclose that certain long chain substitutions onto an estrogenic nucleus may result in compositions exhibiting antiestrogenic activity.

For a number of years, there has been search for compounds which can efficiently inhibit androgen and-/or estrogen formation without causing adverse effects to healthy tissues. More particularly, the inhibition of 17β-hydroxysteroid dehydrogenase, which is involved in the biosynthesis of testosterone, androst-5-ene-3β,17β-diol and estradiol, has been studied by some workers. Some affinity-label inhibitors for human placental estradiol 17β-dyhydrogenase have been described (c. C. Chin and J. C. Warren, J. Biol. Chem. 250, 7682-7686, 1975; Y. M. Bhatnager et al. J. Biol. Chem. 253, 811-815, 1978; C. C. Chin et al., J. Biol. Chem. 255, 3660-2664, 1980; J. L. Thomas and R. C. Strickler, J. Biol. Chem. 258, 1587-1590, 1983).

B. Tobias et al., J. Biol Chem. 257, 2783-2786, 1982 and R. J. Auchus and D. F. Covey, Biochemistry 25, 7295-7300, 1986 disclose, respectively, the use of 17β-propynyl-substituted progestins and propynyl-substituted 3-hydroxy-14,15-secoestra-1,3,5(10)-trien-17-one as inhibitors of the 17β-estradiol dehydrogenase.

Thomas J. L. et al., J. Biol. Chem. 258, 11500, 1983 have described that 16-methylene estradiol and 16-methylene estrone are inhibitors of 17β-hydroxysteroid dehydrogenase activity.

OBJECTS OF THE INVENTION

It is an object of the present invention to provide methods of inhibiting sex steroid activity. Such methods may be useful in the treatment of sex steroid-activity diseases.

It is another object of the invention to provide a steroidal pure antiestrogen for therapeutic use.

It is another object of the invention to provide compositions capable of inhibiting sex steroid synthesis, especially estrogen synthesis.

It is another object to provide an antiestrogen having good affinity for estrogen receptors, but substantially lacking undesirable agonistic activity regarding these receptors and substantially lacking hormonal activity.

It is another object of the invention to provide a therapeutic antiestrogenic composition useful in the treatment of estrogen-related diseases. These diseases include, but are not limited to, breast cancer, uterine cancer, ovarian cancer, endometriosis, uterine fibroma, precocious puberty and benign prostatic hyperplasia.

It is another object of the invention to provide inhibitors of sex steroid production useful in the treatment of both estrogen- and androgen-related diseases. Androgen-related diseases include but are not limited to prostate cancer, acne vulgaris, hirsutism, precocious puberty, benign prostatic hyperplasia, seborrhea, androgenic alopecia and sexual deviants. Control of androgen activity may also be useful in male contraception.

SUMMARY OF THE INVENTION

The present invention provides a method of inhibiting sex steroid activity in a warm-blooded animal, including humans, comprising administering to said animal a therapeutically effective amount of a compound having as part of its molecular structure an estrogenic nucleus of general structure I:

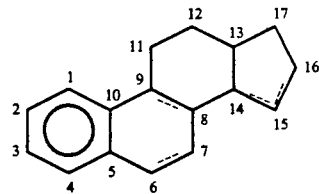

wherein the dotted lines represent optional pi bonds and wherein said compound includes as another part of its molecular structure a side chain substituents onto a ring carbon of said general structure I represented by the formula —R$^1$[—B—R$^2$—]$_x$L—G wherein at least one of said side chains is substituted at a ring carbon selected from the group consisting of carbon 14, carbon 15, carbon 16 and carbon 17, wherein:

x is an integer from 0 to 6, wherein at least one of L and G is a polar moiety distanced from said ring carbon by at least three intervening atoms, and wherein:

R$^1$ and R$^2$ are independently either absent or selected from the group consisting of straight- or branched-chain alkylene, straight- or branched-chain alkynylene, straight- or branched-chain alkenylene, phenylene, and fluoro-substituted analogs of the foregoing;

B is either absent or selected from the group consisting of —O—, —S—, —Se—, —SO—, —SO$_2$—, —NR$^3$—, —SiR$^3$$_2$—, —CR$^3$OR$^3$—, —NR$^3$CO—, —NR$^3$CS—, —CONR$^3$—, —CSNR$^3$—, —COO—, —COS—, —SCO—, —CSS—, —SCS—, —OCO— and phenylene (R$^3$ being hydrogen or lower alkyl);

L is either a moiety which together with G, forms a heterocyclic ring having at least one nitrogen atom or is selected from the group consisting of lower alkyl, —CONR$^4$—, —CSNR$^4$—, —NR$^5$CO—, —NR$^5$CS—, —NR$^5$CONR$^4$—

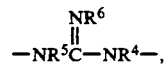

—SO$_2$NR$^4$—, —CSS—, —SCS—, —(NO)R$^4$—, —(PO)R$^4$—, —NR$^5$COO—, —NR$^5$SO$_2$—, —O—, —NR$^4$—, —S—, —SO— and —SO$_2$— (R$^4$ and R$^5$ being independently selected from the group consisting of hydrogen and lower alkyl; and R$^6$ being selected from the group consisting of hydrogen, nitrile and nitro); and G is either a moiety which together with L forms a heterocyclic ring having at least one nitrogen atom, or is selected from the group consisting of hydrogen, lower alkyl, lower alkenyl, lower alkynyl, (C$_3$-C$_7$)cycloalkyl, bromo)lower)alkyl, chloro(lower)alkyl, fluoro(lower)alkyl, iodo(lower)alkyl, cyano(lower)alkyl, carboxy(lower)alkyl, (lower)alkoxycarbonyl(lower)alkyl, (C$_6$-C$_{10}$)aryl, (C$_7$-C$_{11}$)arylalkyl, di(lower)alkylamino(lower)alkyl and fluoro-substituted analogs of the foregoing.

The invention further provides a method of inhibiting sex steroid activity in a warm-blooded animal, including humans, comprising administering a therapeutically effective amount of at least one compound having, as part of its molecular structure, a substituted or unsubstituted estrogenic nucleus of general structure I:

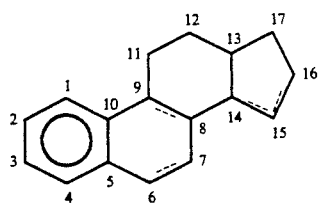

wherein the dotted lines represent optional pi bonds; and wherein said compound includes as another part of its molecular structure a side chain substituted onto a ring carbon of said general structure I in at least one position selected from the group consisting of 7, 11, 14, 15, 16, 17, (preferably 7α, 15α, or 17α), a side chain of the formula —R$^1$[—B—R$^2$—]$_x$L—G, as defined above, and wherein general structure I further includes at least one substitution selected from the group consisting of 15-halo, 16-halo, 14-hydroxyl, 15-hydroxyl, 14-lower alkyl, 15-lower alkyl (and halogenated or cyano derivatives of foregoing), 14-nitro, 15-nitro, 16-nitro, 14-alkoxy, 15-alkoxy, 16-alkoxy, 14-alkyl (or dialkyl) amino, 15-alkyl (or dialkyl) amino, 16-alkyl (or dialkyl) amino, 14-cyano, 15-cyano, 16-cyano, a 15,16 bridge atom (preferably carbon) a 14,15 bridge atom (preferably oxygen), 16-pi-bonded lower alkyl and 16-pi-bonded lower halogenated alkyl.

Chloro- or bromo-substitution at the 16 position is preferred. A pi-bonded lower alkyl substitution at 16 is believed to increase efficacy of compounds utilized in the foregoing methods, as in an alkynyl substitution at the 17α position. In preferred embodiments R$^{17}$ is hydroxyl or in some embodiments R$^{17\alpha}$ and R$^{17\beta}$ together are=0.

The present invention further provides methods for the treatment of sex steroid-related diseases by administering therapeutically effective amounts of sex-steroid activity inhibitors as disclosed herein (with or without pharmaceutical carriers or diluents). Sex steroid-related diseases include any disease whose onset, maintenance or progress is, at least in part, dependent upon biological activities induced by sex steroids such as androgens and estrogens. For example, androgen-dependent diseases include but are not limited to prostate cancer, acne vulgaris, hirsutism, precocious puberty, benign prostatic hyperplasia, seborrhea, androgen alopecia and sexual deviance. Control of androgenic activity may also be useful in male contraception. Estrogen-related diseases include but are not limited to breast cancer, uterine cancer, ovarian cancer, endometriosis, uterine fibroma, precocious puberty and benign prostatic hyperplasia.

The invention further provides a pharmaceutical composition comprising a pharmaceutically acceptable diluent or carrier and a therapeutically effective amount of a sex steroid activity inhibitor having an estrogenic nucleus of formula I:

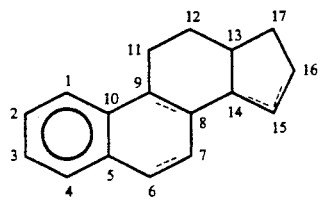

substituted at a ring carbon with at least one side chain represented by the formula —R$^1$[—B—R$^2$—]$_x$L—G where the constituents of said side chain, the location (and preferred locations) for said chain, and the preferred structures and substituents of said nucleus are as defined in the above methods for inhibiting sex steroid activity.

The invention further provides a sex steroid activity inhibiting compound having an estrogenic nucleus of formula I:

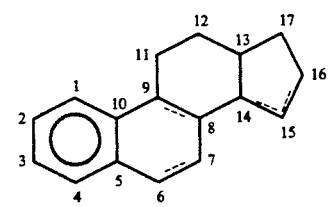

substituted at a ring carbon with at least one side chain represented by the formula —R$^1$[—B—R$^2$—]$_x$L—G wherein the constituents and locations (and preferred locations) of said chain, and the preferred structure and substituents of said nucleus are as defined above for the methods of inhibiting sex steroid activity.

The invention further provides an inhibitor of sex steroid activity having, as part of its molecular structure, a substituted or unsubstituted non-steroidal estrogenic nucleus of general formula II:

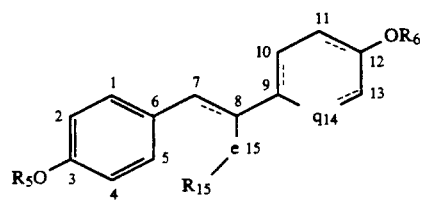

wherein

R$^5$ and R$^6$ are hydrogen lower alkyl, alkoxy carbonyl, (C$_1$-C$_{20}$) alkanoyl, (C$_3$-C$_{20}$)alkenoyl, (C$_3$-C$_{20}$) alkynoyl, (C$_7$-C$_{11}$) aroyl and alkylsilyl, wherein dotted lines are optional pi bonds. In some embodiments, the optional pi bonds are not simultaneously present when aromaticity would result from such simultaneous presence, wherein R$^{15}$ is either a direct bond from e to the number 5 carbon or a methylene or ethylene linkage to the number 5 carbon or a lower alkyl substituent, wherein e is selected from the group consisting of carbon, sulfur and nitrogen, q is absent or is a divalent methyl or ethyl moiety; said inhibitor further having a side cain of the formula —R$^1$]—B—R$^2$—]$_x$ L—G wherein in at least one of said side chains is substituted at position selected from the group consisting of carbon 2, carbon 4, carbon 5, carbon 10, carbon 11, carbon 13, q and on e atom wherein:

x is an integer from 0–6, wherein at least one of L and G is a polar moiety distanced from said ring carbon by at least three intervening atoms, and wherein:

R$^1$ and R$^2$ are independently either absent or selected from the group consisting of straight- or branched-chain alkylene, straight- or branch-carbon 2, carbon 4, carbon 5, carbon 10, carbon 11, q and on e atom wherein:

x is an integer from 0 to 6, wherein at least one of L and G is a polar moiety distanced from said ring carbon by at least three intervening atoms, and wherein:

$R^1$ and $R^2$ are independently either absent or selected from the group consisting of straight- or branched-chain alkylene, straight- or branched-chain alkynylene, straight- or branched-chain alkenylene, phenylene, and fluoro-substituted analogs of the foregoing;

B is either absent or selected from the group consisting of —O—, —S—, —Se—, —SO$_2$—, —NR$^3$—, —SiR$^3{}_2$—, —CR$^3$OR$^3$—, —NR$^3$CO—, —NR$^3$CS—, —CONR$^3$—, —CSNR$^3$—, —COO—, —COS—, —S-CO—, —CSS—, —SCS—, —OCO— and phenylene ($R^3$ being hydrogen or lower alkyl);

L is either a moiety which together with G, forms a heterocyclic ring having at least one nitrogen atom or is selected from the group consisting of lower alkyl, —CONR$^4$—, —CSNR$^4$—, —NR$^5$CO—, —NR$^5$CS—, —NR$^5$CONR$^4$—

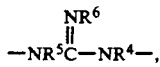

—SO$_2$NR$^4$—, —CSS—, —SCS—, —(NO)R$^4$—, —(PO)R$^4$—, —NR$^5$COO—, —NR$^5$SO$_2$—, —O—, —NR$^4$—, —S—, —SO— and —SO$_2$— (R$^4$ and R$^5$ being independently selected from the group consisting of hydrogen and lower alkyl; and R$^6$ being selected from the group consisting of hydrogen, nitrile and nitro); and G is either a moiety which together with L forms a heterocyclic ring having at least one nitrogen atom or is selected from the group consisting of hydrogen, lower alkyl, lower alkenyl, lower alkynyl, (C$_3$-C$_7$)cycloalkyl, bromo(lower)alkyl, chloro(lower)alkyl, fluoro(lower)alkyl, iodo(lower)alkyl, cyano(lower)alkyl, carboxy(lower)alkyl, (lower)alkoxycarbonyl(lower)alkyl, (C$_6$-C$_{10}$)aryl, (C$_7$-C$_{11}$)arylalkyl, di(lower)alkylamino(lower)alkyl, fluoro-substituted analogs of the foregoing.

This invention further provides a pharmaceutical composition comprising a pharmaceutically acceptable diluent or carrier and a therapeutically effective amount of a sex steroid activity inhibitor having, as part of its molecular structure, a substituted or insubstituted estrogenic nucleus of general structure II,

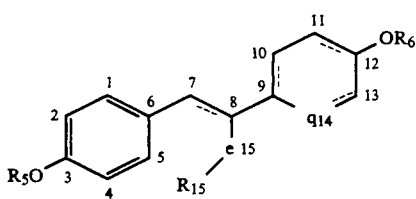

wherein dotted lines are optional pi bonds; wherein e is selected from the group consisting of carbon, sulfur and nitrogen, q is absent or selected from the group consisting of a divalent methyl moiety and a divalent ethyl moiety; $R^{15}$ is selected from the group consisting of a lower alkyl substituent, a direct bond from e to the number 5 carbon, a methyl linkage from e to the number 5 carbon; said sex steroid inhibitor further including, as another part of its molecular structure, a side chain substitution onto at least one positive said general structure II wherein said side chain has the general formula —R$^1$[—B—R$^2$—] L—G as denifed above.

The inhibitor is preferably hydroxy substituted in at least the 3 or 12 positions, and is preferably substituted at the 7 position with a C$_1$-C$_4$ alkyl. Compounds of formula II above may be used, preferably as part of pharmaceutical compositions including acceptable diluents or carriers, to treat sex steroid dependent diseases by inhibiting sex steroid activity.

As used herein, the term "sex steroid activity inhibitor" includes any compound which suppresses the activity of sex steroids by any mechanism including, for example, inhibition of sex steroid synthesis or antagonistic blocking of sex steroid receptors. "Androgen activity inhibitors" and "estrogen activity inhibitors" are sex steroid inhibitors capable of inhibiting the activity of androgens and estrogens, respectively. For example, estrogen activity inhibitors include, but are not limited to antiestrogens which block estrogen receptors, thereby making them unavailable to estrogen compounds which could otherwise activate those receptors. Sex steroid activity inhibitors also include compounds which inhibit the formation of compounds capable of activating sex steroid receptors such as inhibitors of the production of natural sex steroids (e.g. 17$\beta$-estradiol) or inhibitors of production of precursors of natural sex steroids. One mechanism by which these sex steroid production inhibitors may operate is by blocking enzymes which catalyze production of natural sex steroids or their precursors (e.g. enzymes such as aromatase, 17$\beta$-hydroxysteroid dehydrogenase, 3$\beta$-hydroxysteroid dehydrogenase and the like).

As used herein, the term "estrogenic nucleus" includes any compound which, in the absence of the side chain substituent specified herein, is capable of acting as an estrogen as determined by a weight increase of at least 100 percent over a seven-day period of the uterus of ovariectomized rats treated with the compound in question (0.5 mg twice daily per 100 grams of body weight) versus a control group of ovariectomized rats. Treatment should start on the day of castration. The precise test, other than any parameters set forth in this paragraph, is that reported in Simard et al., Mol. Endocrinol. 2: 775–784 (1988).

The following conventions apply to structural formulae set forth herein. Unless specifically designated to the contrary, substituents may have either $\alpha$ or $\beta$ stereochemistry or, where valence permits may represent one substituent in $\alpha$ position and another in $\beta$ position. Presence of optional pi bonds are independent of each other. All structures include salts thereof. Atoms of any estrogenic nucleus for which no substituent is shown or described may optionally be substituted or unsubstituted so long as such substitution does not prevent the nucleus from functioning as an "estrogenic nucleus" as defined herein. Those atoms having a defined substituent may optionally be further substituted by other substituents where their valence permits such further substitution. As used herein, the term "lower", when describing a chemical moiety means a moiety having 8 or fewer atoms. For instance, a "lower alkyl" means a C$_1$ to C$_8$ alkyl. Any moiety of more than two atoms may be straight- or branched-chain unless otherwise specified.

DETAILED DESCRIPTION OF THE PREFERRED EMBODIMENTS

Figure 1:
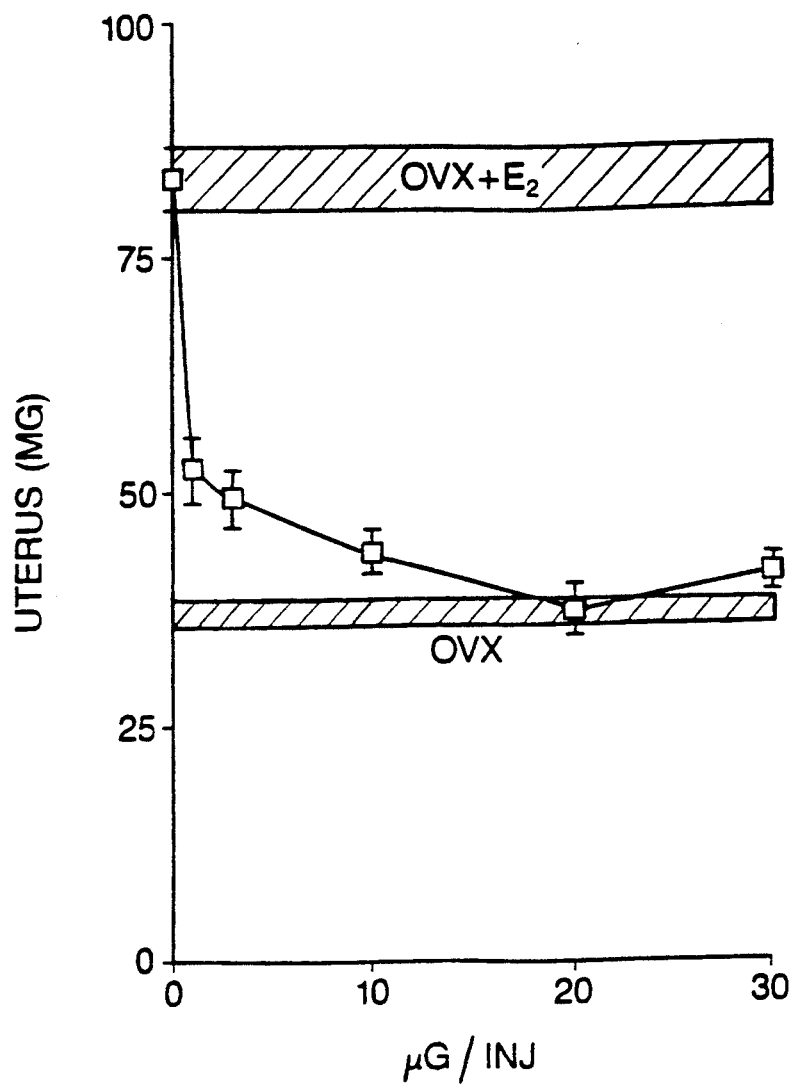
FIG. 1 is a graph illustrating the antiestrogenic activity of one preferred antiestrogen of the invention.

Preferred methods of treating of sex steroid-related diseases, especially estrogen-related diseases, and preferred methods of blocking estrogen receptors comprise administering to a patient in need of such treatment, a therapeutically effective amount of a sex steroid-activity inhibitors as defined above.

Preferred estrogenic nuclei suitable for use in accordance with the invention include but are not limited to estradiol and derivatives thereof. Other suitable estrogenic nuclei include but are not limited to those which (as reported in the references set forth below) effect more than the threshold increase in uterine weight of ovariectomized rats set forth above as defining an estrogenic nucleus (Simard et al., Mol. Endocrinol. 2: 775-784 (1988)).

Some preferred estrogenic nuclei include but are not limited to:

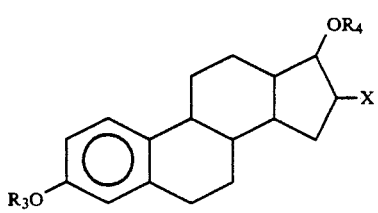

wherein x is a halogen, preferably chlorine or bromine;

wherein $R_3$ and $R_4$ are independently selected from the group consisting of hydrogen, lower alkyl, lower alkoxy carbonyl, ($C_1$-$C_{20}$), alkanoyl, ($C_3$-$C_{20}$) alkenoyl, ($C_3$-$C_{20}$) alkynoyl and ($C_7$-$C_{11}$) aroyl, alkylsilyl, 1-alkyloxy-alkyl and 1-alkyloxy cycloalkyl.

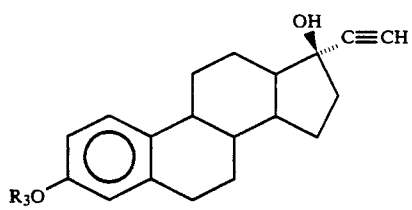

wherein $R_3$ is selected from the group consisting of hydrogen, lower alkyl, lower alkoxy carbonyl, ($C_1$-$C_{20}$), alkanoyl, ($C_3$-$C_{20}$) alkenoyl, ($C_3$-$C_{20}$) alkynoyl and ($C_7$-$C_{11}$) aroyl, alkylsilyl, 1-alkyloxy-alkyl and 1-alkyloxy cycloalkyl.

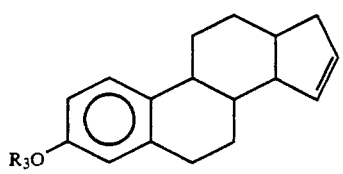

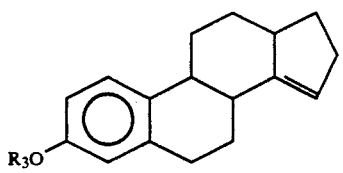

wherein $R_3$ is selected from the group consisting of hydrogen, lower alkyl, lower alkoxy carbonyl, ($C_1$-$C_{20}$), alkanoyl, ($C_3$-$C_{20}$) alkenoyl, ($C_3$-$C_{20}$) alkynoyl and ($C_7$-$C_{11}$) aroyl, alkylsilyl, 1-alkyloxy-alkyl and 1-alkyloxy cycloalkyl.

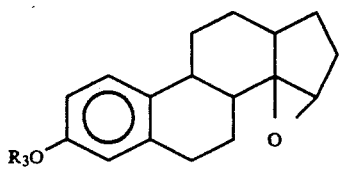

wherein $R_3$ is selected from the group consisting of hydrogen, lower alkyl, lower alkoxy carbonyl, ($C_1$-$C_{20}$), alkanoyl, ($C_3$-$C_{20}$) alkenoyl, ($C_3$-$C_{20}$) alkynoyl and ($C_7$-$C_{11}$) aroyl, alkylsilyl, 1-alkyloxy-alkyl and 1-alkyloxy cycloalkyl.

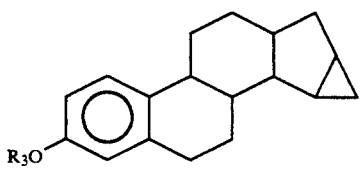

wherein $R_3$ is selected from the group consisting of hydrogens, lower alkyl, lower alkoxy carbonyl, ($C_1$-$C_{20}$), alkanoyl, ($C_3$-$C_{20}$) alkenoyl, ($C_3$-$C_{20}$) alkynoyl and ($C_7$-$C_{11}$) aroyl, alkylsilyl, 1-alkyloxy-alkyl and 1-alkyloxy cycloalkyl.

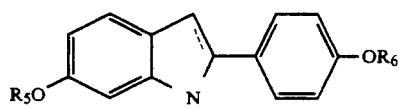

wherein the dotted lines are optional double bonds;
wherein $R_5$ and $R_6$ are independently selected from the group consisting of hydrogen, lower alkyl, lower alkoxy carbonyl, ($C_1$-$C_{20}$), alkanoyl, ($C_3$-$C_{20}$) alkenoyl, ($C_3$-$C_{20}$) alkynoyl and $C_7$-$C_{11}$) aroyl, alkylsilyl, 1-alkyloxy-alkyl and 1-alkyloxy cycloalkyl.

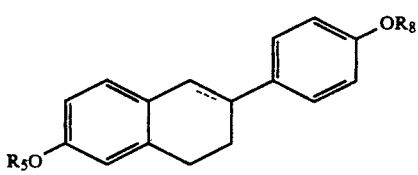

wherein the dotted lines are optional double bonds;
wherein $R_5$ and $R_6$ are independently selected from the group consisting of hydrogens, lower alkyl, lower alkoxy carbonyl, ($C_1$-$C_{20}$), alkanoyl, ($C_3$-$C_{20}$) alkenoyl, ($C_3$–$C_{20}$) alkynoyl and ($C_7$–$C_{11}$) aroyl, alkylsilyl, 1-alkyloxy-alkyl and 1-alkyloxy cycloalkyl.

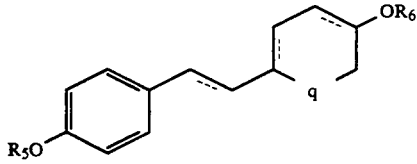

wherein q is absent, methylene or ethylene wherein $R_5$ and $R_6$ are independently selected from the group consisting of hydrogens, lower alkyl, lower alkoxy carbonyl, ($C_1$–$C_{20}$), alkanoyl, ($C_3$–$C_{20}$) alkenoyl, ($C_3$–$C_{20}$) alkynoyl and $C_7$–$C_{11}$) aroyl, alkylsilyl, 1-alkyloxy-alkyl and 1-alkyloxy cycloalkyl.

Preferred sex steroid activity inhibitors result from substituting estrogenic nucleic with the preferred substituents set forth herein, including the side chain —$R^1$—[B—$R^2$] L—G as defined above. Preferred sex steroid activity inhibitors in accordance with the invention include but are not limited to:

N-n-butyl-N-methyl-11-(16′α-bromo-3′,17′β-dihydroxy-estra-1′,3′,5′(10′)-trien-7′α-yl) undecanamide ("EM 105")

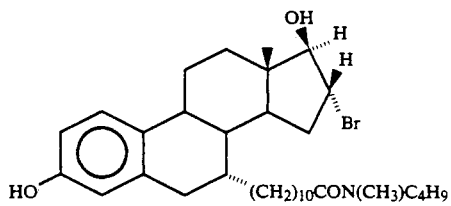

N-n-butyl-N-methyl-11-(16′α-bromo-3′,17′α-dihydroxy-estra-1′,3′,5′(10′)-trien-7′α-yl) undecanamide ("EM 171")

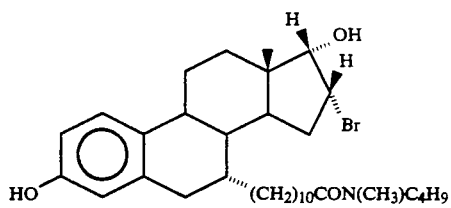

N-n-butyl-N-methyl-11-(16′α-chloro-3′,17′β-dihydroxy-estra-1′,3′,5′(10′)-trien-7′α-yl) undecanamide ("EM 139")

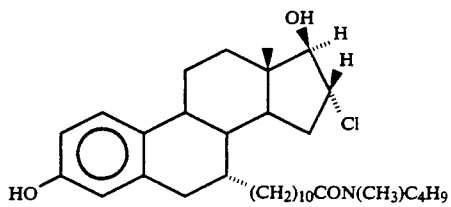

N-n-butyl-N-methyl-11-(16′α-chloro-3′,17′α-dihydroxy-estra-1′,3′,5′(10′)-trien-7′α-yl) undecanamide ("EM 170")

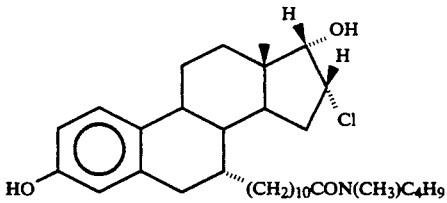

N-n-butyl-N-methyl-11-(16′α-iodo-3′,17′β-dihydroxy-estra-1′,3′,5′(10′)-trien-7′α-yl) undecanamide ("EM 156")

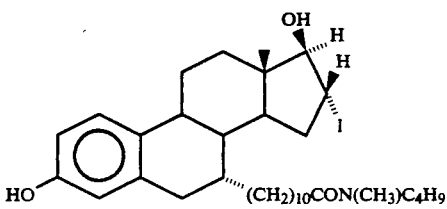

N-n-butyl-N-methyl-11-(3′-hydroxy-17′-oxo-estra-1′,3′,5′(10′),15′-tetraen-7′α-yl) undecanamide ("EM 112")

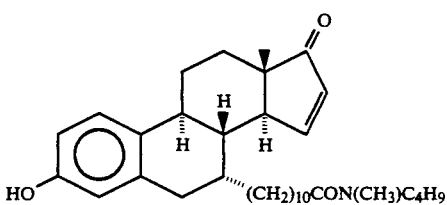

N-n-butyl-N-methyl-11-(3′,17′βdihydroxy-17′α-ethynyl-estra-1′,3′,5′(10′),15′-tetraen-7′α-yl) undecanamide ("EM 123")

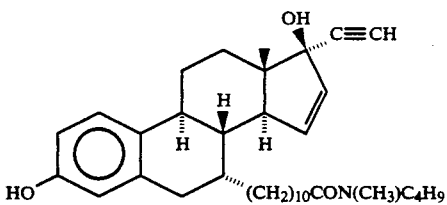

N-n-butyl-N-methyl-11-(3′,17′β-dihydroxy-17′α-ethynyl-estra-1′,3′,5′(10′),14′-tetraen-7′α-yl) undecanamide ("EM 140")

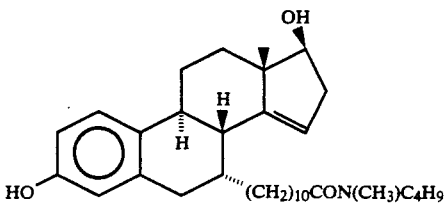

N-n-butyl-N-methyl-11-(3′,17′β-dihydroxy-15′β,16′β-methylene-estra-1′,3′,5′(10′),15′-trien-7′α-yl) undecanamide ("EM 136")

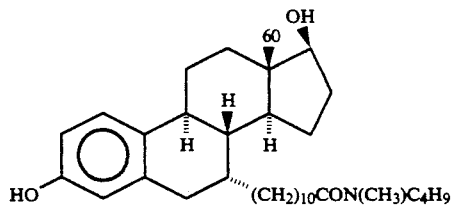

N-n-butyl-N-methyl-11-(3',17'β-dihydroxy-17'α-ethynyl-estra-15'β,16'β-methylene-estra-1',3',5'(10')-trien-7'α-yl) undecanamide ("EM 138")

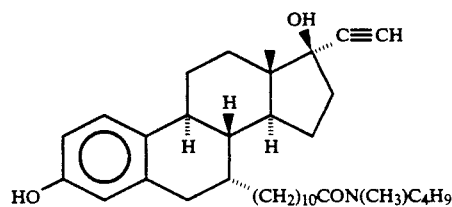

N-n-butyl-N-methyl-11-(3'-hydroxy-15',16'β-methylene-17'oxo-estra-1',3',5'(10')-trien-7'α-yl) undecanamide ("EM 137")

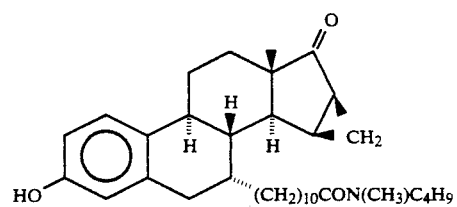

N-n-butyl-N-methyl-11-(3'-hydroxy-16'-methylene-17'oxo-estra-1',3',5'(10')-trien-7α-yl) undecanamide ("EM 175")

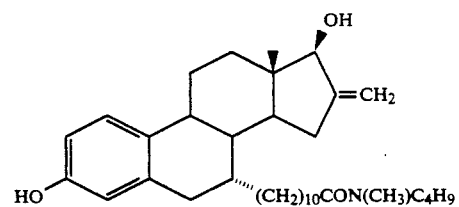

N-n-butyl-N-methyl-11-(3',17'β-dibenzoyl-14'β,15'β-epoxy-estra-estra-1',3',5'(10')-trien-7'α-yl) undecanamide ("EM 180")

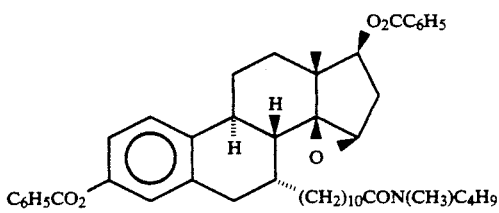

N-n-butyl-N-methyl-11-(3',17'β-dibenzoyl-14'α,15'α-epoxy-estra-estra-1',3',5'(10')-trien-7'α-yl) undecanamide ("EM 181")

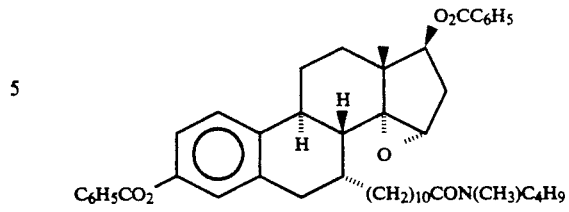

N-n-butyl-N-methyl-11-(3',17'β-dihydroxy-estra-1',3',5'(10')-trien-15'α-yl) undecanamide ("EM 108")

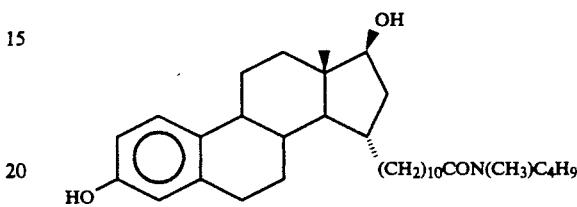

N-n-butyl-N-methyl-13-(3',17'β-dihydroxy-estra-1',3',5'(10')-trien-17'α-yl) 12-tridecynamide ("EM 163")

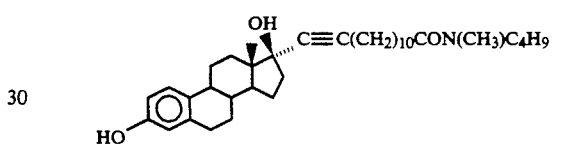

N-n-butyl-N-methyl-14-(3',17'β-dihydroxy-estra-1',3',5'(10')-trien-17'α-yl) 13-tetradecynamide ("EM 195")

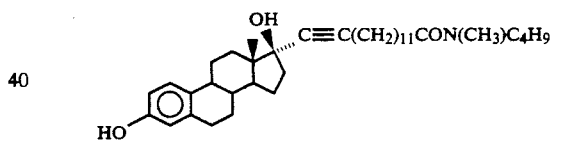

N-n-butyl-N-methyl-8-(3',17'β-dihydroxy-estra-1',3',5'(10')-trien-17'α-yl) 7-octynamide ("EM 157")

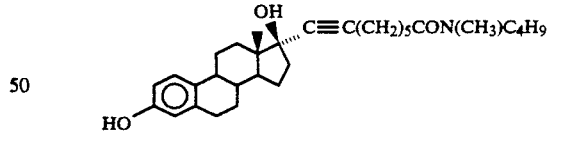

N-n-butyl-N-methyl-11-(6'-hydroxy-2'-(4''-hydroxyphenyl)-3'-ethyl-indole-N'-yl) undecanamide.

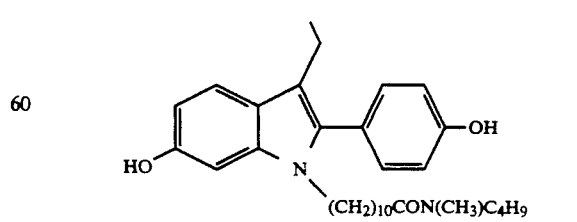

N-n-butyl-N-methyl-11-[6'-hydroxy-2'-(4''-hydroxyphenyl)-(1',2'-dihydronaphtalene-3'-yl)] undecanamide.

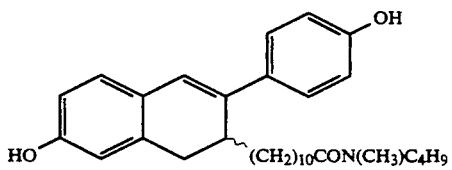

N-n-butyl-N-methyl-11-[4,4'-(1,2-diethyl-1,2-ethanydiyl) bis-phenol-3-yl] undecanamide.

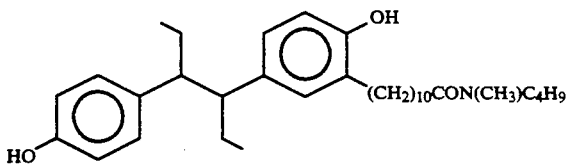

When sex steroid activity inhibitors are administered in accordance with the invention, they are preferably administered as a dosage from about 1 mg to about 2000 mg of active expedient (i.e. sex steroid activity inhibitor), per day per 50 kg of body weight, most preferably from about 10 mg to about 100 mg per day per kg of body weight.

The sex steroid activity inhibitors are preferably prepared as pharmaceutical compositions together with pharmaceutically acceptable carriers and diluents. When prepared for parenteral injection, an inhibitor of sex steroid activity is preferably added at a concentration between about 1 mg/ml and about 100 mg/ml (preferably about 2 mg/ml to about 10 mg/ml) into a carrier preferably selected from the group consisting of saline, water, aqueous ethanol, aqueous dimethylsulfoxide and oil.

When a pharmaceutical composition of the invention is prepared for oral ingestion, the composition preferably includes at least one inhibitor of sex steroid activity wherein the total concentration of all such inhibitors in said pharmaceutical composition is from about 1% to about 95% of the composition (by weight), and preferably from about 5% to about 20%. The composition preferably further includes a pharmaceutically acceptable diluent, for example, starch or lactose with or without tartrazine. Slow release pharmaceutical products comprising the novel inhibitors of sex steroid activity may be incorporated into slow release pharmaceutical products which, other than addition of the novel inhibitors, may be prepared by known methods and administered orally as well as parenterally.

In the side-chain structure, L is preferably separated from the androgenic nucleus by at least 3 intervening and preferably 6 atoms. A polar moiety (G, L or both) is preferably separated from the androgenic nucleus by at least 8 intervening atoms. It is also preferred that the side chain $R^1[-B-R^2-]_x L-G$ have between about 7 and 30 carbon atoms.

EXAMPLES OF SYNTHESIS OF PREFERRED INHIBITORS OF SEX STEROID ACTIVITY

Instrumentation

The IR spectra were taken on a Perkin-Elmer 1310 spectrophotometer. Proton NMR spectra were recorded on a Varian EM-360A (60 MHz, when specified) or a Varian XL-200 (MHz) instrument. The following abbreviations have been used: s, singlet; d, doublet; dd, doublet of doublet; t, triplet; q, quadruplet; and m, multiplet. Chemical shifts are reported in δ values in ppm relative to tetramethysilane (TMS) as internal standard. Mass spectra (MS) were obtained on a V. G. Micromass 16F machine. Thin-layer chromatography (TLC) was performed on 0.25 mm Kieselgel 60F254 plates (E. Merck, Darmstadt, FRG). For flash chromatography, Merck-Kieselgel 60(230–400 mesh A.S.T.M.) was used. All solvents used in chromatography has been distilled. Unless otherwise note, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure. Anhydrous solvents were prepared in the following way.

| SOLVENT | DISTILLED OVER |
|---|---|
| AMINE, DIMETHYLFORMAMIDE | CaH$_2$ |
| HEXANE, DICHLOROMETHANE | P$_2$O$_5$ |
| ACETONE | K$_2$CO$_3$ |
| BENZENE | LiAlH$_4$ |
| TOLUENE | Na |
| ETHER, TETRAHYDROFURAN | LiAlH$_4$, Na Benzophenone |

EXAMPLE 1

SYNTHESIS OF PREFERRED SEX STEROID ACTIVITY INHIBITORS

Synthesis of a starting compound, N-n-butyl, N-methyl-11-(3'-benzoyloxy-17'-oxo-estra-1',3',5'(10')-trien-7α-yl)undecanamide (9) (SCHEME 1)

19-nor-testosterone acetate 3-enolacetate (2)

In an apparatus supplied with a drierite drying tube, a solution of 19-nor-testosterone (1) (100 g; 0.365 mole) in acetic anhydride (200 ml), pyridine (32 ml) and acetylchloride (320 ml) was heated at reflux under magnetic stirring, for 3 h and then concentrated to dryness under vacuum. The dry residue was triturated in absolute ethanol, filtered and washed with little portions of absolute ethanol. After drying, 19-nor-testosterone acetate 3-enolacetate was obtained as a white powder (121.4 g, yield 93%) mp. 176°–177° C. The structure was confirmed by spectroscopic means.

17β-acetoxy-estra-4,6-dien-3-one (3)

To a cooled suspension of enolacetate (121 g; 0.337 mole) in a mixture of DMF (330 ml) and water (7.2 ml) at 0° C. was added, under nitrogen, over a period of 1 h, N-bromosuccinimide (63 g). The resulting solution was stirred for an additional 0.5 h at 0° C. Then lithium carbonate (60.8 g) and lithium bromide (30.4 g) were added. The mixture was heated at 95° C. for 3 h and then poured into 1.7 l of ice-cold water containing 165 ml of glacial acetic acid. After stirring during 15 hours, the crude 17β-acetoxy-estra-4,6-dien-3-one (3) was filtered, washed with water, dried in a desiccating apparatus and recrystallized twice from isopropyl ether (72 g, yield 68%, mp 110° C.). The structure was configured by spectroscopic means.

7α-(11'-acetoxy-undecyl) 17β-acetoxy estra-4-en-3-one (4)

A. Preparation of reagents and solvents 11-bromo undecanol tetrahydro pyranyl ether 11-bromo-undecanol (100 g, 398 mmol) was dissolved in dry ether (768 ml) and the solution was cooled to 0° C. using an ice/H$_2$O bath. To this solution was added HCl gas (2.13 g, 58.4 mmol, 26 ml of HCl/ether).

To this mixture, a solution of 3,4-dihydro-2H-pyran (39.9 g, 43.3 ml) freshly distilled in dry ether (218 ml) was added over a period of 90 min. The solution was then stirred over a period of 16 hours at room temperature. Afterwards, sodium bicarbonate was added to the mixture. The residue was filtered and the solvent was evaporated under vacuum.

The product was then filtered through basic alumina (250 g, Woelm, grade II) using petroleum ether (30-60) as solvent (112 g, 81%).

B. Grignard reagent

In a dry three-neck flask 1000 ml) under dry argon, magnesium (12.0 g, 494 mmol) was placed and activated with iodine. Magnesium was heated with the flame to remove iodine and to dry the apparatus. The system was then cooled to −20° C., and a solution of 11-bromo-undecanol tetrahydro pyranyl ether (73.8 g, 211 mmol) in dry THF (420 ml) was added dropwise. The mixture was stirred under dry argon during one day at −20° C.

The mixture was cooled to −35° C. (±2° C.) using a dry ice/CCL$_4$/acetone bath. The anhydrous cuprous chloride (1.18 g, 12 mmol) was added and the mixture was stirred over a period of 0.5 h.

C. Addition of Grignard reagent

After 0.5 h, using the same apparatus mentioned above (Ar, −35° C.), a solution of 17 β-acetoxy estra-4,6-diene-3-one (3) (32.0 g, 102 mmol) in dry THF (300 ml) was added dropwise over a period of 6 h to the Grignard reagent (red coloration appeared and disappeared). The mixture was stirred for an additional 1 h and, after removal the cooling bath, acidified (about 0° C.) with acetic acid (40 ml), diluted with water and extracted with ether (3×). The ether solution was washed with a saturated sodium bicarbonate solution and water. The organic layer was dried over anhydrous magnesium sulfate and evaporated under reduced pressure to dryness.

The residue was dissolved in MeOH (60 ml) and 5N HCl (180 ml), refluxed for 1 h and 45 min, then concentrated under reduced pressure and cooled in an ice bath. The mixture was then filtered to remove the white precipitate. After the solution had been diluted with water and extracted with methylene chloride (3×), the organic layer was dried over anhydrous MgSO$_4$ and evaporated under reduced pressure to dryness. Finally, the product (55.9 g brown oil) was chromatographed on silica gel (Kieselgel 60F254, Merck, 0.063-0.200 mm, 1500 g). Elution with mixtures of methylene chloride and ethyl acetate (4:1 to 1:2 v/v) and then pure ethyl acetate gave crude 7α-(11'-hydroxy-undecyl)-17β-hydroxy estra-4en-3-one (34.8 g) which was dissolved in dry pyridine (200 ml) and dry acetic anhydride (200 ml), stirred 17 h at room temperature and then poured in ice-water. The product was extracted with methylene chloride (3×), washed with 1N hydrochloric acid, water, saturated sodium bicarbonate and water (3×), dried on anhydrous magnesium sulfate and filtered. After evaporation of solvent, the mixture (35 g) of 7α- and 7β-diacetoxyenones and degradation products of Grignard reagent were separated by flash chromatography on silica gel (Kieselgel 60, Merck, 230 mesh ASTM, 2.0 kg) developed with a mixture of hexane and diethyl ether (2:3 v/v). The first product eluted was pure amorphous 7α-(11'-acetoxy undecyl) 17β-acetoxy-estra-4-en-3-one, (4) (20.8 g, 39.4 mmol, yield from dienone was 39.0%). Further elution gave the 7 β-isomer (5) (5.4 g, 10.3 mmol, 10%). All structures were determined by spectroscopic means.

7α-(11'-hydroxy-undecyl) estra-1,3,5(10)-trien-3,17β-diol (6a)

Under dry argon, a solution of 7α-(11'-acetoxy undecyl) 17β-acetoxy-estra-4-en-3one (4) (17.0 g, 32.4 mmol) in dry acetonitrile (150 ml) was added rapidly to a suspension of cupric bromide (14.8 g, 66.2 mmol) and mmol) and lithium bromide (2.89 g, 33.6 mmol) in warm acetonitrile (75 ml). The mixture was heated to reflux over a period of 30 min and stirred vigorously, and then cooled to room temperature. A saturated aqueous solution of sodium bicarbonate (50 ml) was added, and then the organic compound was extracted with ethyl acetate (3×150 ml). The organic layers were washed with water, dried over anhydrous magnesium sulfate, filtered and evaporated under vacuum to dryness. The residue was chromatographed on silica gel (Kieselgel 60F254 Merck 0.063-0.200 mm; 1000 g). Elution with hexane-ethyl acetate (1:1 v/v) gave the 7α-(11'-acetoxy-undecyl) estra-1',3',5'(10')-trien-3,17β-diol, 17β-acetate (6b) (8.51 g; 50.3%) and the starting product (1.33 g; 15%).

The above diacetate phenol (8.51 g, 16.2 mmol) was dissolved in methanol (90 ml) and sodium hydroxyde 30% (w/v) (9 ml). The mixture was refluxed for 90 min under dry nitrogen. The solution was then concentrated under vacuum and diluted with hydrochloric acid (10% v/v). The mixture was extracted using ethyl acetate (4×150 ml) and the ethyl acetate extract was washed with water, dried over anhydrous magnesium sulfate, filtered and evaporated under vacuum. The evaporation gave 7α-(11'-hydroxy undecyl) estra-1,3,5(10)-trien-3,17β-diol (6a) (6.99 g, 98% brut) as a yellow foam, the structure of which was confirmed by spectroscopic means.

3-benzoyloxy 7α-(11'-hydroxy undecyl) estra-1,3,5(10)-trien-17β-ol (7)

The above triol (6.99 g; 15.8 mmol) was dissolved in acetone (25 ml) and an aqueous solution of sodium hydroxyde (1N, 19.1 ml). The mixture was cooled to 0° C. using an ice/water beth. Benzoyl chloride (2.22 ml, 19.1 mmol) was then added dropwise. The mixture was stirred for 40 min at 0° C. and then diluted with water. The solution was extracted using ethyl acetate (3×) and the organic layers were washed with a saturated aqueous solution of sodium bicarbonate and finally with water. The ethyl acetate solution was dried over anhydrous magnesium sulfate, filtered and evaporated under vacuum to dryness. Then, the residue was immediately chromatographed on silica gel (Kieselgel, 60F254, 0.063-0.200 mm; 500 g). The chromatography was carried out, first, using methylene chloride as solvent (about 1 liter) and secondly the pure 3-benzoyloxy 7α-(11'-hydroxy undecyl) estra-1,3,5(10)-trien-17β-ol (7), colorless oil (6.50 g, 75%) was eluted with methylene chloride-ethyl acetate (5:1 about 1 liter and 4:1; v/v). The structure was confirmed by spectroscopic means.

11-(3'-benzoyloxy-17'-oxo-estra-1',3',5'(10')-trien-7'α-yl) undecanoic acid (8)

To a cooled solution of 3-benzoyloxy-7α-(11'-hydroxy undecyl)estra-1,3,5(10)-trien-17β-ol (7) (4.3 g) in acetone (100 ml) was added dropwise Jone's reagent (8N-chromic acid solution, 6.7 ml). After 30 min, isopropanol (40 ml) was added and the mixture was concentrated under vacuo. Water was added and the mixture was extracted four times with ethyl acetate. The organic layers were washed twice with brine, dried over magnesium sulfate and evaporated to dryness. The crude 11-(3'-benzoyloxy-17'-oxo-estra-1',3'5'(10')-trien-7'α-yl) undecanoic acid (8) (3.94 g) was used in the next step without purification.

N-n-butyl, n-methyl-11-(3'-hydroxy-17'-oxo-estra-1',3',5'(10')-trien-7'α-yl) undecanamide (9b)

To 11-(3'-benzoyloxy-17'-oxo-estra-1',3',5'(10')-trien-7'α-yl) undecanoic acid (8) (3.94 g, 7.22 mmol), dissolved in anhydrous $CH_2Cl_2$ (100 ml) and cooled at $-10°$ C. was added tributylamine (2.18 ml, 9.15 mmol) and isobutylchloroformate (1.30 ml, 10.0 mmol). The solution was stirred during 35 min. and N-methylbutylamine (13 ml, 109.7 mmol) was added. The mixture was warmed to room temperature and stirred during 1 h. Afterward, $CH_2Cl_2$ was added and the organic phase was washed with 1N HCl, water, saturated sodium bicarbonate solution and finally with water, dried with anhydrous $MgSO_4$ and the solvent was removed under reduced pressure. The residue was purified by chromatography on silica gel. Elution with mixture of EtOAc/hexane (1.5:8.5 v/v) yielded N-butyl, N-methyl-11-(3'-

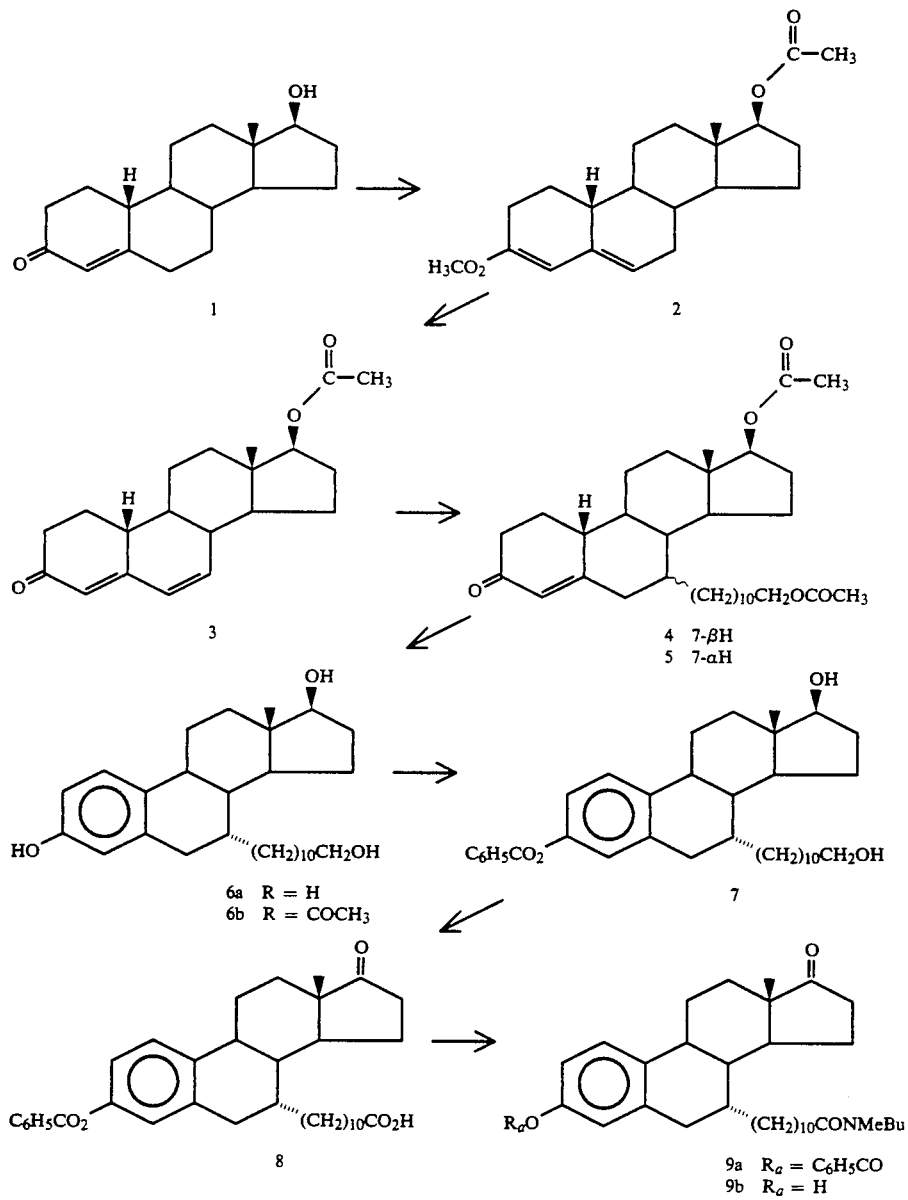

Scheme 1 benzoyloxy-17'-oxo-estra-1',3',5'(10')-trien-7'α-yl) undecanamide (9a) (4.25 g, 96%) as colorless oil; IR ν (neat)1750, 1725 and 1640 cm$^{-1}$. The above described benzoyloxy amide 9341 mg, 0.54 mmol) was dissolved in methanol (10 ml) and cooled at 0° C. Following this 2N NaOH (5 ml) was added and the mixture was stirred during 60 min. at 0° C. The solution was neutralized with 1N HCl and extracted with CH$_2$Cl$_2$. The organic phase was dried with anhydrous MgSO$_4$ and the solvent was removed under reduced pressure. The residue was purified by chromatography on silica gel. Elution with mixture of EtOAc/hexane (3:7 v/v) yielded N-butyl, N-methyl-11-(3'-hydroxy-17'-oxo-estra-1',3',4'(10)-trien-7'α-yl) undecanamide (9b) (284 mg, 97%) as colorless oil; $^1$H-NMR δ (CDCl$_3$) 0.91 (s, 3H, 18'-CH$_3$), 2.76 app (d, 1H J=16.3 Hz, part of ABX system, 6'-H) 2.96 and 2.98 (2s, 3H, N—CH$_3$), 3.27 and 3.38 (2t$_{app}$, 2H, J=7.5 Hz, N—CH$_2$—), 6.63 (broad s, 1 H, 4'-H), 6.70 (broad d, 1H, J=8.5 Hz, 2'-H), 7.123 (d, 1H, J=8.4 Hz, 1'-H); IR ν$_{max}$ (neat) 3270, 1730, 1615 cm$^{-1}$; MS m/e 523 (M$^+$, 100%), 508 (M$^+$-CH$_3$, 32%), 142 (C$_2$H$_4$CON(CH$_3$)C$_4$H$_9$$^+$, 47%).

16-Halo-Estradiol Undecanamide (Scheme 2)

N-n-butyl, N-methyl-11-(3',17'-diacetoxy-estra-1',3',5'(10'),16'-tetraen-7'α-yl) undecanamide (10)

The ketone amide 9b (163 mg, 0.50 mmol) was dissolved in isoprenyl acetate (10 ml). p-toluenesulfonic acid (44 mg) was then added and the solution was distilled about two-thirds of the original volume in 7 h and was then stirred at reflux for 12 h. Afterwards, the solution was cooled with an ice-water bath and extracted with 50 ml of cooled ether. The ether was washed with a cooled satured sodium bicarbonate and water. The organic phase was dried with anhydrous MgSO$_4$ and the solvent was removed under reduced pressure. The residue was filtered through alumina (15 mm×50 mm alumina Woehlm neutral, activity II) using a mixture of benzene-diethyl ether (3:7 v/v) as eluant. The solvent was removed under reduced pressure and, the residue was purified by flash chromatography on silica gel. Elution with mixture of EtOAc/hexane (1:4 v/v) yielded the N-butyl, N-methyl-11-(3',17'-diacetoxy-estra-1',3',5'(10'), 16'-tetraen-7'α-yl) undecanamide (10) (244 mg, 80%) as colorless oil; $^1$H-NMR δ$_m$(CDCl$_3$) 0.92 (s, 3H, 18'-CH$_3$), 0.92 and 0.95 (2t, 3H, J=7.0 Hz, N(CH$_2$)$_3$CH$_3$), 2.18 (s, 3H, 17'-OCOCH$_3$), 2.28 (s, 3H, 3'-OCOCH$_3$), 2.76 app (d 1H, J=16.1 Hz, part of ABX system, 6'-H), 2.90 and 2.96 (2s, 3H, N—CH$_3$), 32.6 and 3.35 (2t$_{app}$, 2H, J=7.6 Hz, N—CH$_2$—), 5.52 (m, 1H, 16'-H), 6.80 (broad, s, 1H, 4'-H), 6.85 (dd, 1H, J$_1$=9.1 Hz and J$_2$=3.0 Hz, 2'-H), 7.27 (d, 1H, J=9.1 Hz, 1'-H); IR ν$_{max}$(neat) 1750, 1635, 1200 cm$^{-1}$; MS m/e 607 (M$^+$, 2%), 5 (M$^+$-COOH$_2$, 100%), 550 (M$^+$-COCH$_2$—CH$_3$, 13%), 523 (M$^+$-2COCH$_2$, 45%), 142 (C$_2$H$_4$CON(CH$_3$C$_4$H$_9$$^+$, 55%), 129 (C$_4$H$_9$(CH$_3$)NCOCH$_3$$^+$, 38%), 114 (C$_4$H$_9$(CH$_3$)NCO$^+$, 60%), 86 (C$_4$H$_9$(CH$_3$)N$^+$, 25%); EXACT MASS calcd for C$_{36}$H$_{57}$N 607.4239, found 607.4234.

N-butyl, N-methyl-11-(16'α-chloro-3'acetoxy-17'-oxo-estra-1',3',4'(10')-triene-7'α-yl) undecanamide (11, X=Cl)

To diacetate amide 10, dissolved in 5 ml of acetone, was added a solution of sodium acetate (2.6 equivalents) in acetic acid and water (1:11.3 v/v) and then, was treated with tertbutyl hypochlorite (1 eq.) prepared from t-butanol (4 ml) and Javel water (Javex 6.1%, 50 ml). The clear solution was warmed to 55° C. and stirred for 1 h. Afterwards, the solvent was evaporated to dryness. The residue was dissolved in ether (100 ml) and water was added (20 ml). The organic phase was washed with water, dried with anhydrous MgSO$_4$ and evaporated to dryness. The residue was purified by chromatography on silica gel carried out with mixture of EtOAc/hexane (3:7 v/v) to give the N-butyl, N-methyl-11-(16'α-chloro-3'-acetoxy-17'-oxo-estra-1',3',4'(10')-trien-7'α-yl) undecanamide 11, X=Cl) (115 mg, 89%) as colorless oil; $^1$H-NMR ν (CDCl$_3$) 0.92 and 0.95 (2t, 3H, J=7.0 Hz, N(CH$_2$)$_3$CH$_3$), 0.96 (s, 3H, 18'-CH$_3$), 2.28 (s, 3H, 3'-OCOCH$_3$), 2.80 app (d, 1H, J=16.6 Hz, part of ABX system, 6'-H) 2.90 and 2.96 (2s, 3H, N—CH$_3$), 3.24 and 3.35 (2t$_{app}$, 2H, J=7.4 Hz, —N—CH$_2$—), 4.46 (d, 1H, J=6.6 Hz, 16'β-H), 6.82 (broad s, 1H, 4'-H), 6.86 (dd, 1H, J=9.1 Hz and J$_2$=2.6 Hz, 2'-H), 7.29 (d, 1H, J=9.1 Hz, 1'-H); IR ν$_{max}$ (neat) 1750, 1640, 1205 cm$^{-1}$; MS m/e 601, 599 (M$^+$, 24%, 68%), 142 (C$_2$H$_4$CON(CH$_3$)C$_4$H$_9$$^+$, 100%), 114 (C$_4$H$_9$(CH$_3$)NCO$^+$, 93%).

N-butyl, N-methyl-11-(16α-chloro-3',17'-dihydroxy-estra-1',3',5'(10')-trien-7'α-yl) undecanamide ("EM 139") and ("EM170")

A stirred solution of haloketone amide (11, X=Cl) in anhydrous tetrahydrofuran (THF) (10 ml) under argon was chilled to −70° C. with 2-propanol/dry ice bath. A solution of 1.0M of lithium aluminium hybride (2 eq.) was then added dropwise. After 30 min, the reaction was allowed to return slowly at 0° C. for 5 min, then was quenched by the dropwise addition of a mixture of THF-EtOAc (5 ml) (1:1 v/v) and acidified at pH~4 with (10%) HCl. The mixture was stirring for 5 min at room temperature and then extracted with EtOAc. The organic phase was washed with water, dried on anhydrous Na$_2$SO$_4$ and evaporated under reduced pressure. The residue was chromatographed on silica gel with a mixture of EtoOAc/hexane (4:6 v/v) as eluant:

N-butyl, N-methyl-11-(16'α-chloro-3'17'α-dihydroxy-estra-1',3',5'(10')-trien-7'α-yl) undecanamide ("EM 170")

(15 mg, 29%) as colorless oil; analytical sample was obtained by HPLC purification; $^1$H-NMR δ (CDCl$_3$, 400 MHz) 0.79 (s, 3H, 18'-CH$_3$), 0.93 and 0.96 (2t, 3H, J=7.3 Hz, N(CH$_2$)$_3$CH$_3$), 2.80 (2H, J$_{6,6}$=17.1 Hz and J$_{6,7}$=4.5 Hz, Δδ=24.34 (Hz, system ABX, 6'-H), 2.94 and 2.99 (2s, 3H, N—C$_3$), 3.26 (dd, J$_1$=7.6 Hz and J$_2$=7.4 Hz) and 3.32-3.43 (m)-[2H, —N—CH$_2$—], 3.71 (d, 1H, J=4.5 Hz, 17'β-H), 4.63 (ddd, 1H, J$_{16,15}$=10.2 Hz, J$_{16,17}$=4.5 Hz and J$_{16,15}$ 3.9 Hz, 16'β-H), 6.50 (d, 1H, J=24 Hz, 3'-OH), 6.60 (d, 1H, J=2.5 Hz, 4'-H), 6.66 (dd, 1H, J$_1$=8.4 Hz and J$_2$=2.5 Hz, 2'-H), 7.14 (d, 1H, J=8.5 Hz, 1'-H); IR ν$_{max}$ (neat) 3300, 1615, 1495 cm$^{-1}$; MS m/e 561,559 (M$^+$, 40%, 100%), 523 (M$^+$-HCl, 20%), 142 (C$_2$H$_4$CON(CH$_3$)C$_4$H$_9$$^+$, 44%), 114 (C$_4$H$_9$(CH$_3$)CNO$^+$, 37%); Exact mass calculated for C$_{34}$H$_{54}$O$_3$N$^{35}$Cl 559.3785, found 559.3821.

N-butyl, N-methyl-11-(16'α-chloro-3',17'β-dihydroxy-estra-1',3',5'(10')-trien-7'α-yl) undecanamide ("EM 139")

(25 mg, 55%) as a colorless oil; analytical sample was obtained by HPLC purification; 1H-NMR δ (CDCl$_3$, 400 MHz), 0.81 (s, 3H, 18'-CH$_3$), 0.93 and 0.96 (2t, 3H, J=7.3 Hz, (CH$_2$)$_3$CH$_3$), 2.78 (2H, J$_{6,6}$=16.2 Hz and J$_{6,7}$=4.5 Hz, Δ$^5$=24.34 Hz, system ABX, 6'-H), 2.94 and 2.99 (2s, 3H, N—CH$_3$), 3.27 (dd, J$_1$7.6 Hz and J$_2$=7.5 Hz) and 3.31–3.45 (M) [2H, —N—CH$_2$—], 3.86 (dd, 1H, J$_{17,17}$OH=.34 Hz and J$_{17,16}$=5.9 Hz, 17'α-H), 4.11 (ddd, 1H, J$_{16,15}$=10.8 Hz, J$_{16,17}$=5.9 Hz and 4.11 (ddd, 1H, J$_{16,15}$=10.8 Hz, J$_{16,17}$=5.9 Hz and J$_{16,16}$=2.5 Hz, 4'-H), 6.66 (dd, 1H, J=19.7 Hz, 3'-OH), 6.61 (d, 1H, J=2.5 Hz, 4'-H), 6.66 (dd, 1H, J$_1$=8.4 Hz and J$_2$=2.6 Hz, 2'-H), 7.13 (d, 1H, J=8.4 Hz, 1'-H); IR ν$_{max}$ (neat) 3320, 1615, 1490 cm$^{-1}$; MS m/e 561,559 (M$^+$, 38%, 100%), 523 (M$^+$HCl, 16%), 142 (C$_2$H$_4$CON(CH$_3$)C$_4$H$_9^+$, 80%), 114 (C$_4$H$_9$(CH$_3$)NCO$^+$, 76%); exact mass calculated for C$_{34}$H$_{54}$O$_3$N$^{35}$Cl 559.3785, found 559.3825.

N-n-butyl, N-methyl-11-(16'α-bromo-3'-acetoxy-17'-oxo-estra-1',3',5'-(10'),trien-7'α-yl) undecanamide (11, X=Br)

To the above diacetate 10 (244 mg, 0.40 mmol) dissolved in 10 ml of acetic acid was added dropwise with stirring within 10 minutes and at room temperature, a brominating solution composed of 50 mg (0.6 mmol) of sodium acetate, 1.6 ml of acetic acid, 0.04 ml of water and 63.9 mg (0.02 ml, 0.40 mmol) of bromine. During the course of this reaction, a red coloration appeared and disappeared. To the solution, 50 ml of ether was added and the organic phase was washed with water (4×50 ml) followed by a saturated sodium bicarbonate solution (2×50 ml) and finally with water (3×50 ml). The combined phase was dried over anhydrous magnesium sulfate and the solvent was removed in vacuo. The residue was chromatographed on silica gel (Kieselgel, 60F254, Merck, 0.063–0.200 mm). Elution with a mixture of hexane-ethyl acetate (4:1 v/v) yielded N-butyl, N-methyl-11-(16α-bromo-3'-acetoxy-17'-oxo-estra-1',3',5'(10'),trien-7'-α-yl) undecanamide (11, X=Br) (201 mg, 78%) as colorless oil (201 mg, 78%), as colorless oil; 1H-NMR o (CDCl$_3$), 0.94 (s, 3H, 18'-CH$_3$), 2.28 (s, 3H, 3'-OCOCH$_3$), 2.82 app (d, 1H, J=16.4 Hz, part of ABX system, 6'-H), 2.90 and 2.96 (2s, 3H, N—CH$_3$), 3.24 and 3.35 (2t$_{app}$, 2H, J=7.7 Hz, —N—CH$_2$—), 4.58 (t, 1H, J=3.6 Hz, 16β-H), 6.82 (broad s, 1H, 4'-H), 6.88 (dd, 1H, J=8.0 Hz and J$_2$=4.0 Hz, 2'-H), 7.29 (d, 1H, J=8.0 Hz, 1'-H); MS m/e 644 (M$^+$, 7%), 565 (M$^+$-Br, 77%), 522 (M$^+$-Br—COOH$_2$, 55%), 142 (C$_2$H$_4$CON(CH$_3$)C$_4$H$_9^+$, 67%), 114 (C$_4$H$_9$(CH$_3$)NCO$^+$, 66%), 88 (100%).

N-butyl, N-methyl-11-(16α-bromo-3',17'-dihydroxy-estra-1',3,4'(10'-trien-7'α-yl) undecanamide ("EM 105") and "EM 171"

A solution of bromoketone amide 11 (X=Br) (295 mg, 0.46 mmol) in anhydrous tetrahydrofuran (10 ml) under argon was chilled to −70° C. and a solution of 1.0M of lithium aluminium hybride in ether (0.92 ml,

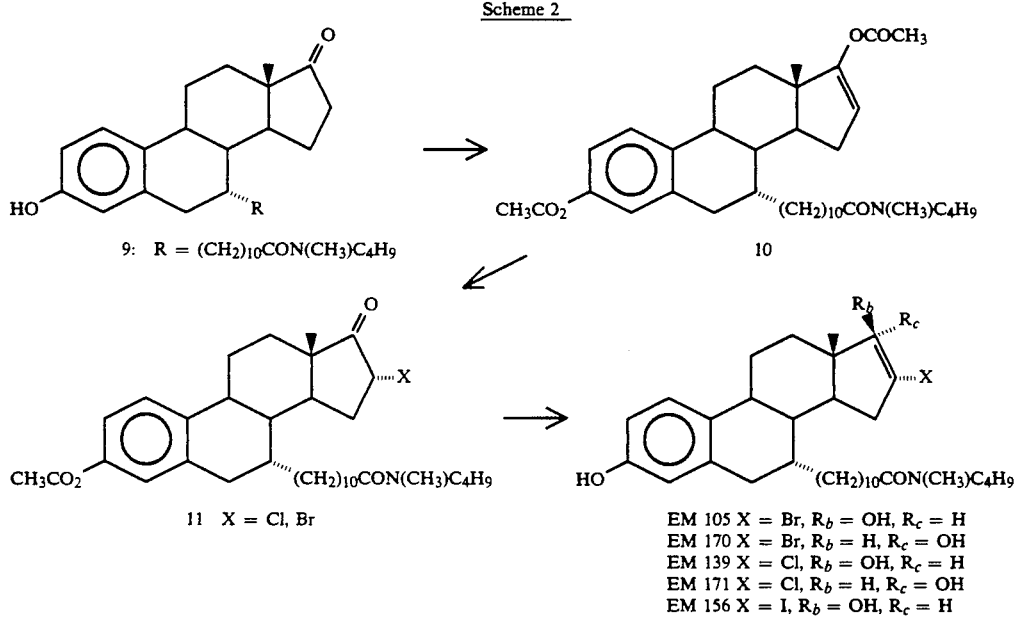

Scheme 2

9: R = (CH$_2$)$_{10}$CON(CH$_3$)C$_4$H$_9$

10

11 X = Cl, Br

EM 105 X = Br, R$_b$ = OH, R$_c$ = H
EM 170 X = Br, R$_b$ = H, R$_c$ = OH
EM 139 X = Cl, R$_b$ = OH, R$_c$ = H
EM 171 X = Cl, R$_b$ = H, R$_c$ = OH
EM 156 X = I, R$_b$ = OH, R$_c$ = H 0.92 mmol) was added dropwise with rapid magnetic stirring. After 30 min, the reaction was quenched by the dropwise addition of mixture of THF-ethyl acetate (1:1 v/v) and acidified by 10% hydrochloric acid. The mixture was stirring for 5 min at room temperature and then extracted with ethyl acetate. The organic phase was washed with water, dried on anhydrous sodium sulfate and evaporated to dryness under reduced pressure. The residue was purified by chromatography on silica gel. Elution with a mixture of hexane-ethyl acetate (7:3 v/v) gave:

N-n-butyl, N-methyl11-(16'α-bromo-3',17'α-dihydroxy-estra-1',3',5'(10'-trien-7'α-yl) undecanamide ("EM 171")

(63 mg, 21%) as colorless oil, $^1$H-NMR δ (CDCl$_3$, 400 MHz) 0.81 (s, 3H, 18'-CH$_3$), 0.93 and 0.96 (2t, 3H, J=7.3 Hz, N(CH$_2$)$_3$CH$_3$), 2.79 (2H, J$_{6,6}$=16.6 Hz, J$_{6,7}$=4.7 Hz, =Δδ=24.34 Hz, system ABX, 6'-H), 2.94 and 2.99 (2s, 3H, N—CH$_3$), 3.27 (dd, 2H, J$_1$=7.7 Hz and J$_2$=7.5 Hz, —N—CH$_2$—), 3.31-3.44 (m, 2H, —N—CH$_2$—), 3.66 (dd, 1H, J$_{17,17}$=1.4 Hz, J$_{17,16}$=4.3 Hz, 17'$\beta$-H), 4.68 (dt, 1H, J$_{16,17}$4.3 Hz, m, J$_{16,15}$=9.7 Hz, 16'$\beta$-H), 6.60 (d, 1H, J=2.4 Hz, 4'-H), 6.65 (dd, 1H, J=8.5 Hz and J$_2$=2.5 Hz, 2'-H), 7.14 (d, 1H, J=8.5 Hz, 1'-H); IR $\nu_{max}$ (neat) 3300, 1615, 1495 cm$^{-1}$; MS m/e 605,603 (M$^+$, 17%), 523 (M$^+$-HBr, 81%), 142 (C$_2$H$_4$CON(CH$_3$)C$_4$H$_9$$^+$, 100%), 114 (C$_4$H$_9$(CH$_3$)NCO$^+$, 97%); Exact mass calculated for C$_{34}$H$_{54}$O$_3$N$^{79}$Br 603.8289, found 603.3304.

N-n-butyl, N-methyl-11-(16'$\alpha$-bromo-3',17'$\beta$-dihydroxy-estra-1',3',5'(10')-trien-7$\alpha$-yl) undecanamide ("EM 105")

(170 mg, 50%) as a colorless oil; analytical sample was obtained by HPLC purification; $^1$H-NMR $\delta$ (CDCl$_3$, 400 MHz), 0.80 (s, 3H, 18, -CH$_3$), 0.93 and 0.96 (2t, 3H, J=7.3 Hz, N(CH$_2$)$_3$CH$_3$), 2.80 (2H, J$_{6,6}$=16.4, J$_{6,7}$=4.6 Hz, $\Delta\delta$=24.34 Hz, system ABX, 6'-H), 2.94 and 2.99 (2s, 3H, N—CH$_3$), 3.27 (dd, 2H, J$_1$=7.7 Hz and J$_2$=7.5 Hz, —N—CH$_2$—), 3.31-3.45 (m, 2H, —N—CH$_2$—), 4.02 (dd, 1H, J$_{17,17}$=3.7 Hz, and J$_{17,16}$=6.1 Hz, 17'$\alpha$-H), 4.15 (ddd, 1H, J$_{16,15}$=10.2 Hz, J$_{16,17}$=6.1 Hz and J$_{16,15}$=2.9 Hz, 16'$\beta$-H), 6.61 (d, 1H, J=2.5 Hz, 4'-H), 6.66 (dd, 1H, J=8.4 Hz and J$_2$ 2.5 Hz, 2'-H), 7.12 (d, 1H, J=8.4 Hz, 1'-H); IR $\nu_{max}$(neat) 3320, 1610, 1490 cm$^{-1}$; MS m/e 605, 603 (M$^+$, 29%), 523 (M$^+$-HBr, 100%0, 142 (C$_2$H$_4$CON(CH$_3$)C$_4$H$_9$$^+$, 70%), 114 (C$_4$H$_9$(CH$_3$NCO$^+$, 60%); Exact mass calculated for C$_{34}$H$_{54}$O$_3$N$^{79}$Br 603.3289, found 603.3289.

N-butyl, N-methyl-11-(16'$\alpha$-iodo-3',17'$\beta$-dihydroxy-estra-1',3',5'(10')-trien-7'$\alpha$-yl) undecanamide ("EM 156")

Under argon atmosphere, a mixture of 16$\alpha$-bromodiol EM 105 (55 mg, 0.91 ) mmol) and dry sodium iodide (136 mg, 0.91 mmol) in freshly ethyl methyl ketone (25 ml) was refluxed in darkness during 12 h. Afterwards, the solvent was evaporated, water was added and the product was extracted with ethyl acetate. The organic phase was washed with 5% sodium thiosulfate and with water, dried over anhydrous sodium sulfate and concentrated to dryness and under reduced pressure. The residue was purified by chromatography. Elution with a mixture of hexane-ethyl acetate (1:1, v/v) gave a mixture of starting material and iodo compound (52:48) of which HPLC separation afforded N-butyl, N-methyl-11,(16'-$\alpha$-iodo-3', 17'$\beta$-dihydroxy-estra-1',3',5'(10')-trien-7'$\alpha$-yl) undecanamide ("EM 156") (21 mg, 36%) as colorless oil; $^1$H-NMR $\delta$ (CDCl$_3$, 400 MHz) 0.78 (s, 3H, 18'-CH$_3$), 0.93 and 0.96 (2t, 3H, J=7.3 Hz, N(CH$_2$)$_3$CH$_3$), 2.79 (2H, J$_{6,6}$=16.5 Hz, J$_{6,7}$=4.4 Hz, $\Delta\delta$, =24.34 Hz, system ABX, 6'-H), 2.94 and 2.99 (2s, 3H, N—CH$_3$), 3.27 (dd, 2H, J$_1$=7.6 Hz and J$_2$=7.5 Hz, —N—CH$_2$) 3.32-3.44 (m, 2H N—CH$_2$), 4.09-4.17 (m, 2H, 16'$\beta$H and 17$\alpha$-H), 6.60 (d, 1H, J=2.4 Hz, 4'-H), 6.65 (dd, 1H, J=8.4 Hz and J$_2$=2.4 Hz, 2'-H), 7.13 (d, 1H, J=8.4 Hz, 1'-H); IR $\nu$ (neat) 3310, 1610, 1490 cm$^{-1}$; MS m/e 651 (M$^+$, 8%), 523 (M$^+$-HI, 100%), 508 (M$^+$-HI-CH$_3$, 38%) 142 (C$_2$H$_4$CON(CH$_3$)C$_4$H$_9$$^+$, 54%), 114 (C$_4$H$_9$(CH$_3$)NCO$^+$, 49%); Exact mass calculated for C$_{34}$H$_{54}$O$_3$NI-HI 523.4028, found 523.4028.

Efficacy of an antiestrogen synthesized in accordance with Example 1

Compound "EM 139" synthesized as shown in Scheme 2 above is an estrogen activity inhibitor. "EM 139" has been tested both for efficacy in acting as an antiestrogen by blocking estrogen receptors without substantially activating those receptors, (see FIG. 1 and explanation below) and for efficacy in inhibiting 17$\beta$-hydroxysteroid dehydrogenase, (see FIG. 2 and explanation below) an enzyme which catalyzes reactions involved in the synthesis of both androgens and estrogens (hereinafter referred to as "17$\beta$-HSD").

The antiestrogenic activity of "EM 139" was measured as shown in FIG. 1 as its ability to inhibit the estradiol-induced stimulation of uterine weight in adult female ovariectomized Balb/c mice (body weight=-19-20 g) sacrificed five days after ovariectomy. Ovariectomized mice injected with estradiol and no antiestrogen had a resultant uterine weight as shown by the shaded area designated "OVX +E$_2$" in FIG. 1. The baseline uterine weight for a control group of ovariectomized mice injected with neither estradiol nor antiestrogen is represented in FIG. 1 by "OVX". The antiestrogen "EM 139", and estradiol dissolved in ethanol were injected subcutaneously in the appropriate test groups in a solution of 0.9% (w/v) sodium chloride and 1% (w/v) gelatin at different concentrations of "EM 139" (as noted along the X axis of FIG. 1.) A dosage of 0.2 ml of the foregoing preparation, was administered twice daily, starting on the day of ovariectomy for a total of 9 injections. Estradiol was injected at the dose of 0.01 $\mu$g in 0.2 ml, twice daily, starting on the morning after ovariectomy for a total of 8 injections.

After sacrifice, the uteri were rapidly removed, freed from fat and connective tissue and weighed. Results shown in FIG. 1 are the means ± SEM of groups of 9-10 mice. As may be seen from FIG. 1, EM 139 was highly potent to reduce estradiol-induced uterine weight gain.

Figure 2:
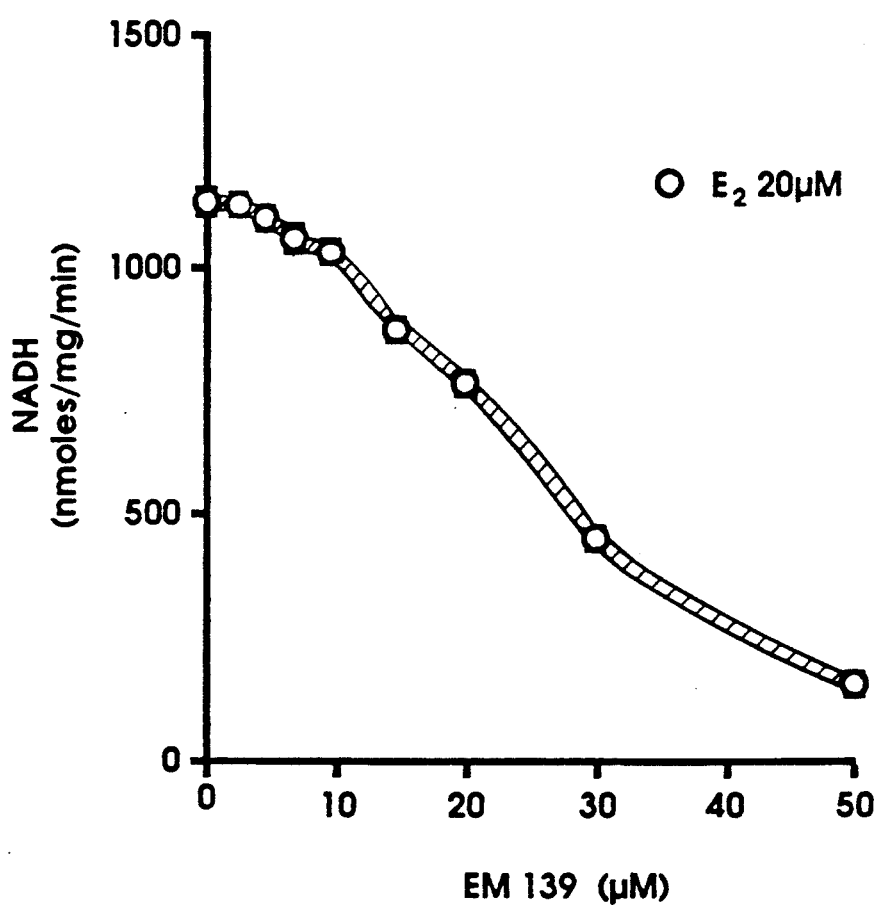
FIG. 2 is a graph illustrating that the antiestrogen which is the subject of FIG. 1 is also a good inhibitor of sex steroid synthesis.

To test the effect of "EM 139" on the inhibition of sex steroid formation, its effect in inhibiting 17'-hydroxysteroid dehydrogenase catalysis (specifically, conversion of estradiol to estrone, was observed. The reaction was followed by monitoring formation of the reduced form of nicotinamide adenine dinucleotide ("NADH") (at 340 nm) because the rate of conversion of cofactor NAD (the oxidized form) to NADH varies directly with the rate of estradiol conversion to estrone. The ability of "EM 139" to inhibit estrone production is indicative of its ability to inhibit the activity of 17'-hydroxysteroid dehydrogenase (Thomas et al. J. Biol. Chem. 258: 11500-11504, 1983). 17$\beta$-hydroxysteroid dehydrogenase (17$\beta$-HSD) was purified to homogeneity from human placenta. A reaction vessel was prepared containing 1 $\mu$g 17$\beta$-HSD, 5 nM NAD, 20 $\mu$M 17$\beta$-estradiol, and the concentrations of the test compound "EM 139" which are indicated along the X-axis of FIG. 2 in 1.0 ml of a mixture of Tris-HCl (50 mM), EDTA (2 mM), NaN$_3$ (5 mM). The pH was 7.5. The reaction was allowed to proceed at 25° C. for 15 min. Formation of NADH was measured at 340 nm. As shown by FIG. 2, increasing concentrations of EM 139 significantly inhibited the reaction (shown in FIG. 2 as a decrease in formation of NADH).

EXAMPLE 2

N-n-BUTYL-N-METHYL-11-(3',17β-DIHYDROXY-17'α-ETHINYL-ESTRA-(1',3',5'(10'), 15'-TETRAEN-7'α-YL) UNDECANAMIDE ("EM 123") (Scheme 3)

N-n-butyl-N-methyl-11-(3'-benzoyloxy-17'-ethylenedioxy estra-1',3',5'(10')-,trien-7'α-yl) undecanamide (12)

A mixture of N-n-butyl, N-methyl-11-(3'-benzoyloxy-17'-oxo estra-1', 3',5'(10')-trien-7'α-yl) undecanamide (9a) (3.63g), ethylene glycol (215 ml), p-toluenesulfonic acid (530 mg) and anhydrous benzene (250 ml) was refluxed with a Dean-Stark apparatus during 24 h. After cooling, the mixture was poured in water and extracted three times with ether. The organic layer was washed with a saturated sodium bicarbonate solution, and brine (3×), dried on magnesium sulfate and evaporated to dryness. The residue was purified by flash chromatography on silica-gel (Kieselgel 60, Merck, 230 mesh ASTM, 300 g). Elution with a mixture of hexane-ethyl acetate (6:4 v/v) gave pure N-butyl, N-methyl-11-(3'-benzoyloxyo-17'-ethylenedioxy estra-1',3',5'(10'), trien-7'α-yl) undecanamide (3.58 g, 92%) as an oil, the structure of which was confirmed by spectroscopic means.

N-n-butyl, N-methyl-11-(3'-benzoyloxy-16'α-bromo-17'-ethylenedioxy-estra-1',3',5'(10'),trien-7'α-yl) undecanamide (13)

TO the above ethylenedioxy amide 12 (370 mg, 0.55 mmol) in anhydrous tetrahydrofuran (10 ml) cooled at 0° C. was added dropwise under argon, a solution of pyridinium bromide perbromide (406 mg, 1.36 mmol) in 7 ml of the same solvent. After stirring during 1.5 h at 0° C., sodium iodide (300 mg) was added and the solution was stirred for 25 min. Afterwards, a solution of sodium thiosulfate (10%, v/v, 10 ml) and pyridine (0.5 ml) was added and the mixture was stirred for an additional 4 h and then poured into water and extracted three times with ether. The organic layers were washed with 1N hydrochloric acid, water, saturated bicarbonate solution and water (3×), dried on magnesium sulfate and evaporated to dryness. The residue was chromatographed on silica-gel (50 g). Elution with a mixture of hexane-ethyl acetate (4:1 v/v) gave pure N-n-butyl, N-methyl-11-(3'-benzoyloxy-16'α-bromo-17'-ethylenedioxy-estra-1',3',5'(10'),trien-7'α-yl) undecanamide (13) (313 mg, 76%) as colorless oil; IR $\nu_{max}$ (neat), 1730, 163 1595 and 1255 cm$^{-1}$; $^1$H NMR, 0.93 (3H, s, 18'-CH$_3$), 2.28 (2H, td, J=7.5 and 2.6 Hz, —CH$_2$CON—), 2.90 and 2.95 (3H, 2s, —N—CH$_3$), 3.24 and 3.35 (2H, 2t, J=7.3 Hz, —N—CH$_2$—), 3.85 and 4.35 (4H, m, —OCH$_2$CH$_2$O—), 4.56 (1H, m, H-C.16'), 6.91 (1H, d, J=2.2 Hz, H-C.4'), 6.98 (1H, dd, J=8.4 and 2.2 Hz, H-C.2'), 7.32 (1H, d, J=8.4 Hz, H-C.1'), 7.49 (2H, t$_{app}$, J=7.0 Hz H-C.3" and H-C.5"), 7.63 (1H, t$_{app}$, J=7.0 Hz, H-C.4") and 8.17 (2H, d, J=7.0 Hz, H-C.2" and H-C.6"), MS m/e, 671 (M+-Br, 11%), 114 (C$_4$H$_9$(CH$_3$)NCO+, 13%), 105 (C$_6$H$_5$CO+, 100%), 86 (C$_4$H$_9$(CH$_3$)N+, 10%), 77 (C$_6$H$_5$+, 25%).

N-n-butyl, N-methyl-11-(3'-hydroxy-17'-oxo-estra-1',3',5'(10'), 15'-tetraen-7'α-yl) undecanamide "(EM 112)"

To a solution of the bromoketal (13) 517 mg, 0.69 mmol) in anhydrous dimethyl sulfoxide warmed at 73° C. under argon, was added potassium-t-butoxide (1.55 g, 13.8 mmol). The mixture was stirred for 5 h at this temperature and then cooled, poured in ice-water, acidified with 1N hydro-chloric acid and extracted three times with ethyl acetate. The organic layers were washed with water (3×), dried on magnesium sulfate and evaporated to dryness. The residue was dissolved in acetone (30 ml), water (7 ml) and p-toluenesulfonic acid (60 mg) was added. The resulting solution was stirred for 5 h at room temperature and then poured into water. The organic compound was extracted three times with ether, washed with a saturated sodium bicarbonate solution and water (3×), dried on magnesium sulfate and evaporated to dryness. The residue was purified by "flash chromatography" (100 g). Elution with a mixture of hexane-ethyl acetate (1:1 v/v) gave the pure N-butyl, N-methyl-11-(3'-hydroxy-17'-oxo-estra-1',3',540 (10'),15'-tetraen-7'α-yl) undecanamide "EM 112" (178 mg, 49%) as colorless oil; IR $\nu_{max}$ (neat), 3290, 1695, 1620 and 1600 cm$^{-1}$; $^1$H NMR, 0.92 and 0.95 (3H, 2t, J=7.3 and 7.0 Hz, —N—(CH$_2$)$_3$ CH$_3$), 1.11 (3H, s, 18'-CH$_3$), 2.32 (2H, td, J=2.5 and 7.0 Hz, H-C.2), 2.94 and 2.99 (3H, 2s, N—CH$_3$), 3.27 and 3.38 (2H, 2t, J=7.7 and 7.3 Hz, —N—CH$_2$—), 6.11 (1H, dd, J=6.2 and 3.3 Hz, H-C.15'), 6.66 (1H, d, J=2.6 Hz, H-C.4'), 6.71 (1H, dd, J=8.4 and 2.6 Hz, H-C.2'), 7.13 (1H, d, J=8.4 Hz, H-C.1'), 7.60 (1H, dd, J=6.2 and 1.5 Hz, H-C.16') and 7.70 (1H, broad s, w$_{\frac{1}{2}}$=16 Hz, OH), MS m/e, 521 (M+, 53%), 507 (M+-CH$_2$, 9%), 506 (M+-CH$_3$, 7%), 142 (C$_2$H$_4$CON(CH$_3$)C$_4$H$_9$+, 25%), 114 (C$_4$H$_9$(CH$_3$)NCO+, 60%) and 86 (C$_4$H$_9$(CH$_3$N+, 22%), 44 (100%).

N-n-butyl, N-methyl-11-(3',17'β-dihydroxy-17'α-ethinyl-estra-1',3',5'(10'),15'-tetraen-7'α-yl) undecanamide ("EM 123")

To hexanes (1 ml) cooled at 0° C., were added trimethylsilylacetylene (0.112 ml), n-butyllithium 1.6M in hexanes (0.25 ml), few drops of anhydrous THF and finally, a slowly addition of a solution of enone amide EM 112 (57 mg) in anhydrous THF (1.2 ml). The mixture was stirred for 30 min at 0° C. After addition of a saturated ammonium chloride solution, the mixture was extracted with ethyl acetate (3×). The organic layers were washed with water and brine, dried over magnesium sulfate and filtered. The solvent was removed under reduced pressure. To the residue (61 mg) dissolved in methanol, a 5N potassium hydroxyde solution (0.177 ml) was added and the mixture refluxed for 50 min. After cooling and addition of a saturated ammonium chloride solution, the mixture was extracted three times with ethyl acetate. The organic layers were washed with brine, dried over magnesium sulfate and filtered. The organic solvent was removed under reduced pressure. The residue was chromatographed on silica-gel (5 g). Elution with a mixture of hexanes: ethyl acetate (7:3 v/v) gave N-butyl, N-methyl-11-(3',17'β-dihydroxy-17'α-ethinyl-estra-1',3',5'(10'),15-tetraen-6'α-yl)undecanamide ("EM 123") (34 mg, 63%); IR $\nu_{max}$ (neat), 3290, 2150, 1620 and 1600 cm$^{-1}$; $^1$H NMR, 0.92 and 0.95 (3H, 2t, J=7.3 and 7.02 Hz, N—(CH$_2$)$_3$CH$_3$), 0.95 (3H, s, 18'-CH$_3$), 2.32 (2H, td, J=7.0 and 2. Hz, —CH$_2$CON—), 2.66 (1H, s, —CH), 2.93 and 2.98 (3H, 2s, N—CH$_3$), 3.27 and 3.38 (2H, t, J=7.0 Hz, —N—CH$_2$—), 5.78 (1H, dd, J=5.9 and 3.3 Hz, H-C.15'), 6.05 (1H, dd, J=5.9 and 1.5 Hz, H-C.16'), 6.62 (1H, d, J=2.5 Hz, H-C.4'), 6.67 (1H, dd, J=8.4 and 2.6 Hz, H-C.2') and 7.13 (1H, d, J=8.4 Hz, H-C.1') ppm;

MS m/e 547 (M+, 12%), 142 (C$_2$H$_4$CON(CH$_3$)C$_4$H$_9$+, 21%) 114 (C$_4$H$_9$(CH$_3$)NCO+, 50%), 88 (100% and 86 (C$_4$H$_9$(CH$_3$)N+, 34%).

EXAMPLE 3

16β-Cyclopropyl Derivatives

N-n-butyl, N-methyl-11-(17′-oxo-3′-hydroxy-15′β,16′β-methylene-estra 1′,3′,5′(10′-trien-7′α-yl) undecanamide (14)

A solution of the phenol-enone EM 112 (101 mg; 0.19 mmol) dissolved in anhydrous pyridine (15 ml) and acetic anhydride (10 ml) was stirred at room temperature for 20 h. The mixture was into ice-water, then extracted three times with ether. The organic layers were washed with 1N hydrochloric acid, water and a saturated sodium bicarbonate solution and water, dried on magnesium sulfate and evaporated to dryness. The residue was purified by "flash chromatography" on silica-gel (20 g). Elution with a mixture of hexane-ethyl acetate (7:3 v/v) gave the N-butyl, N-methyl-11-(17′-oxo-3′-acetoxy-estra-1′,3′,5′(10′),15′-tetraen-7′α-yl) undecanamide.

To this and palladium (II) acetate (11 mg) in ether (25 ml) an ethereal diazomethane solution (prepared from 1 g of diazald) was added dropwise at 0° C. with continuous stirring during 10 min. After evaporation, the residue was dissolved in methanol (50 ml ) and cooled to 0° C. 2N sodium hydroxide solution (1 ml) was added and after 75 min. of stirring the mixture was neutralized with 1N hydrochloric acid, extracted three times with ether. The organic layers were washed with brine, dried on magnesium sulfate and evaporated to dryness. The residue was purified by HPLC to give N-butyl, N-methyl-11-(17′-oxo-3′-hydroxy-15′β,16′β-methylene-estra-1′,3′,5′(10′)-trien-7′α-yl) undecanamide (14) (79 mg, 76%) as a colorless oil. IR $\nu_{max}$ (neat) 3260, 1610 and 1570 cm$^{-1}$; $^1$H NMR (400 MHz) 0.93 and 0.96 (3H, 2t, J=7.3 Hz, N(CH$_2$)$_3$CH$_3$), 0.99 (3H, s, 18′-CH$_3$), 1.98 (1H, td, J=8.3 and 3.96 Hz, H-C.16′), 2.80 (1H, d, J=16.6 Hz, Hβ-C.6′), 2.94 and 2.98 (3H, 2s, N—CH$_3$), 32.7 (1H, dd, J=7.58 and 6.66 Hz) and 3.38 (1H, m) (both are —N—CH$_2$—), 6.64 (1H, d, J=2.6 Hz, H-C.4′), 6.66 (1H, dd, J=8.2 and 2.6 Hz, H-C.3′) and 7.10 (1H, d, J=8.2 Hz, H-C.1′) ppm; MS m/e 535 (M+, 74%), 522 (M+-CH$_2$, 49%), 129 (C$_4$H$_9$(CH$_3$)NCOCH$_3$+, 37%), 114 (C$_4$H$_9$(CH$_3$)NCO+, 67%) and 88 (100%).

N-n-butyl, N-methyl-11-(3′,17′β-dihydroxy-15′β16′β-methylene-estra-1′,3′,5′(10′)-trien-7′α-yl) undecanamide ("EM 136")

To the cyclopropylketone 14 (10 mg, 18.6 μmol) dissolved in methanol (8 ml) was added sodium borohydride (1.5 mg). The mixture was stirred at room temperature for 18 h. After addition of water, the mixture was concentrated under reduced pressure. The residue was diluted with water and extracted three times with ethylacetate. The organic layers were washed with brine, dried over magnesium sulfate and filtered. The organic solvent was removed under reduced pressure and the residue was purified by "flash chromatography" on silica-gel (5 g). Elution with a mixture of hexanes: ethyl acetate (5:5 v/v) gave N-butyl, N-methyl-11-(3′,17′β-dihydroxy 15′β,16′β-cyclopropyl-estra-1′,3′,5′(10′)-trien-7′α-yl) undecanamide ("EM 136"), as a colorless oil; IR $\nu_{max}$ (neat) 3300, 1615, 1580 and 1450 cm$^{-1}$; $^1$H NMR (400 MHz), 0.31 (1H, dd, J=14.0 and 7.8 Hz, H-C.1″) 0.93 (3H, s 18′-CH$_3$), 0.93 and 0.96 (3H, 2t, J=7.3 Hz, N(CH$_2$)$_3$CH$_3$), 2.77 (1H, d, J=17.1 Hz, Hβ-C.6′), 2.94 and 2.98 (3H, 2s, N—CH$_3$, 3.27 (1, dd, J=7.7 and 7.5 Hz) and 3.39 (1H, m) (both are —N—CH$_2$—), 4.09 (1H, broad s, w=10 Hz, H-C.17′), 6.64 (2H, m, H-C.4′ and H-C.2′) and 7.11 (1H, d, J=8.3 Hz, H-C.1′) ppm; MS m/e 537 (M+, 18%), 519 (M+-H$_2$O, 56%), 504 (M+-H$_2$-CH$_3$, 100%), 142 (C$_2$H$_4$CON(CH$_3$)C$_4$H$_9$+, 70%), 114 (C$_4$H$_9$(CH$_3$)NCO+, 50%) and 86 (C$_4$H$_9$CH$_3$)N+, 33%).

N-n-butyl, N-methyl-11-(3′,17′β-dihydroxy-17′α-ethinyl-15′β,16′β-methylene-estra-1′, 3′,5′(10′)-trien-7′α-yl) undecanamide ("EM 138")

To hexanes (500 μl) cooled at 0° C. , were added trimethylsilylacetylene (54.6 μl), 1.6M n-butyl lithium in hexanes (120.4 μl), few drops of anhydrous THF and finally, a slowly addition of a solution of the cyclopropyl ketone "EM 136" (25.8 mg), in anhydrous THF (350 μl). The mixture was stirred for 75 min at 0° C. After addition of a saturated ammonium chlorid solution (1 ml), the mixture was extracted three times with ethyl acetate. The organic layers were washed with water and brine, dried over magnesium sulfate and filtered. The solvent was removed under reduced pressure. To the residue dissolved in methanol (900 μl), a 5N potassium hydroxyde solution (70 μl) was added and the mixture refluxed for 30 min. After cooling and addition of a saturated ammonium chloride solution (1 ml), the mixture was extracted three times with ethyl acetate. The organic layers were with washed with brine, dried over magnesium sulfate and filtered. The organic solvent was removed under reduced pressure. The residue was purified by "flash chromatography" on silica-gel (5 g). Elution with a mixture of hexanes: ethyl acetate (5:5 v/v) gave N-butyl, N-methyl-11-(3′,17′β-dihydroxy-17′α-ethinyl-15′β,16′β-cyclopropyl-estra-1′,3′,5′(10′)-trien-7′α-yl) undecanamide ("EM 138") (12 mg, 44%) as a colorless oil; IR $\nu_{max}$ (neat) 3590, 3300, 1620, 1600 and 1450 cm$^{-1}$; $^1$H NMR (400 MHz), 0.39 (1H, ddd, J=14.6 and 7.9 Hz, H-C.1′), 0.93 and 0.96 (3H, 2t, J=7.4 and 7.3 Hz, —N(CH$_2$)$_3$—CH$_3$), 0.96 (3H, s, 18′-CH$_3$), 2.70 (1H, s, —C≡CH), 2.77 (1H, d, J=16.5 Hz, Hβ-C.6′), 2.94 and 2.98 (3H, s, N—CH$_3$), 3.27 (1H, dd, J=7.7 and 7.6 Hz) and 3.38 (1H, m) (both are N—CH$_2$—), 6.42 (1H, m, OH), 6.65 (2H, m, H-C.4′ and H-C.2′) and 7.12 (1H, d, J=8.3 Hz, H-C. 1′) ppm; MS m/e 561 (M+, 15%), 142 (C$_2$H$_4$CON(CH$_3$)C$_4$H$_9$+, 66%), 114 (C$_4$H$_9$(CH$_3$)CO+, 53%), 88 (100%) and 86 (C$_4$H$_9$(CH$_3$)N+, 35%).

SCHEME 3
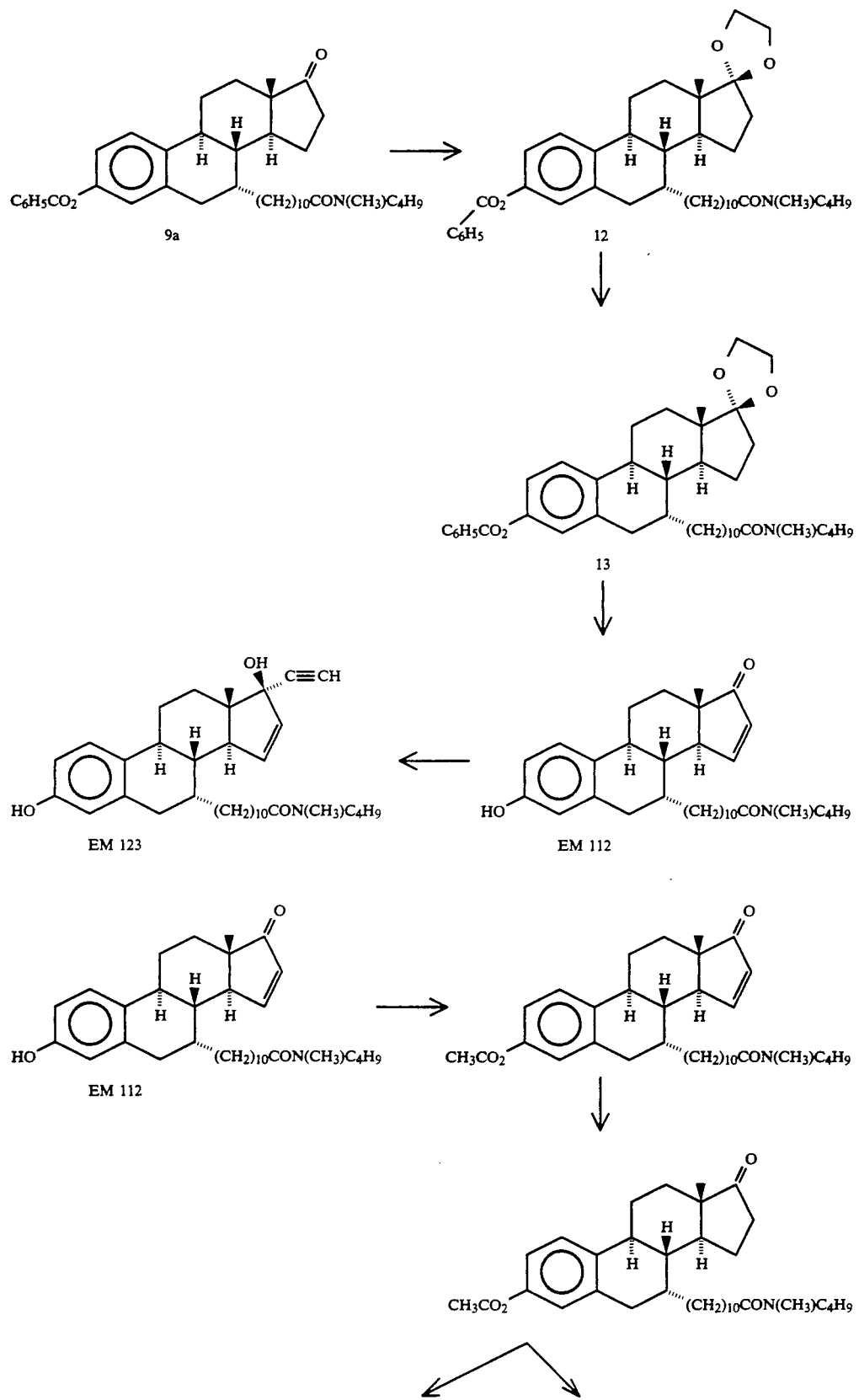

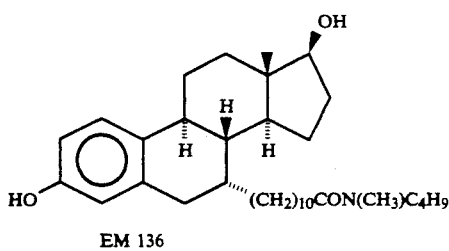

EM 136

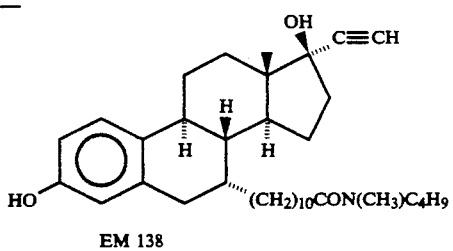

EM 138

17α-ALKYNYLAMIDE ESTRADIOLS

General Procedure for Ester Formation (scheme 4 A)

In anhydrous conditions under argon atmosphere, bromo acid (17 mmol) was dissolved in dry CH$_2$Cl$_2$ (30 ml), oxalyl chloride (12 ml) was added and the reaction was stirred 2 h at room temperature. Then, dry benzene was added to mixture and solvent was evaporated under reduced pressure (2×) and dried under vacuum. This crude product was dissolved in dry CH$_2$Cl$_2$ (20 ml) and added at 0° C. to a solution of 3-methyl 3-oxetanemethanol (17 mmol), CH$_2$Cl$_2$ (7 ml) and pyridine (1.4 ml). The reaction was keeped at this temperature for 4-8 h. Thereafter, mixture was diluted with CH$_2$Cl$_2$, washed with NaHCO$_3$ (10%, w/v) and organic phase was dried over MgSO$_4$. After removal of solvent, residue was purified by chromatography (hexane-ethylacetate-triethylamine/80:20:1, v/v/v) to afford bromo ester.

6-bromo hexanoate ester of 3-methyl-3-hydroxymethyloxetane (15). Light yellow liquid (91% yield); IR ν (neat) 2930, 2860, 1725, 1450, 1370, 1160 cm$^{-1}$; NMR-60 δ (CDCl$_3$) 1.31 (s, 3H), 1.1–2.1 (m, 6H), 2.36 (t, J=6.0 Hz, 2H), 3.36 (t, J=6 Hz, 2H), 4.13 (s, 2H), 4.41 (AB system Δν=8.3, J=6 Hz, 4H).

9-bromo nonanoate ester of 3-methyl-3-hydroxymethyl oxetane (16). Colorless liquid (86% yield); IR ν (neat) 2920, 2840, 1725, 1450, 1370, 1150 cm$^{-1}$; NMR-60 δ (CDCl$_3$) 1.31 (s, 11H), 1.2–2.2 (m, 4H), 2.40 (t, J=6.0 Hz, 2H), 3.45 (t, J=6.0 Hz, 2H), 4.20 (s, 2H), 4.48 (AB system Δν=8.2, J=6.0 Hz, 4H).

11-bromo undecanoate ester of 3-methyl-3-hydroxymethyl oxetane (17). Colorless liquid (85% yield); NMR-60 δ (CDCl$_3$) 1.33 (s, 15H), 1.0–2.0 (m, 4H), 2.30 (t, J=6.0 Hz, 2H), 3.35 (t, J=6.0 Hz, 2H), 4.12 (s, 2H), 4.40 (AB system Δν=8.2, J=6.0 Hz, 4H).

12-bromo dodecanoate ester of 3-methyl-3-hydroxymethyl oxetane (18). Colorless liquid (86% yield); IR ν (neat) 8910, 2840, 1720, 1450, 1370, 1155 cm$^{-1}$; NMR-60 δ (CDCl$_3$) 1.30 (s, 17H), 1.1–2.0 (m, 4H), 2.30 (t, J=6.0 Hz, 2H), 3.33 (t, J=6.0 Hz, 2H), 4.11 (s, 2H), 4.40 (AB system Δν=8.0, J=6.0 Hz, 4H).

General Procedure for Ortho Ester Formation (scheme 4 A)

To a solution of bromo ester (3.4–14.2 mmol) in dry CH$_2$Cl$_2$ (10–40 ml) at 0° C. was added with stirring distilled boron trifluoride etherate (0.85–3.55 mmol). After 4 h at 0.° C. reaction mixture was quenched by the addition of triethylamine (3.4–14.2 mmol), diluted with diethylether and filtered to remove the amine-BF$_3$ complex. The filtrate was evaporated and residue was purified by chromatography (hexane-ethylacetatetriethylamine/80:20:1, v/v/v) to give bromo ortho ester.

1-(5'-bromo pentanyl)-4-methyl-2,6,7-trioxabicyclo [2.2.2] octane 19. Colorless oil (68% yield); IR ν (neat) 2940, 2915, 2855, 1450, 1390, 1050, 980 cm$^{-1}$; NMR-60 δ (CDCl$_3$) 0.79 (s, 3H), 1.2–2.0 (m, 8H), 3.35 (t, J=6.0 Hz, 2H), 3.87 (s, 6H); MS m/e (rel. intensity) 280 (M+, 0.2), 278 (M+; 0.2), 250 (8.1), 248 (8.5), 197 (7.2), 195 (7.7), 179 (58), 177 (61), 72 (54), 69 (100).

1-(8'-bromo octanyl)-4-methyl-2,6,7-trioxabicyclo [2.2.2]octane (20). Amorphous white solid (69% yield); IR ν (KBr) 2940, 2900, 2840, 1450, 1390, 1045, 985, 950 cm$^{-1}$; NMR-60 δ (CDCl$_3$) 0.80 (s, 3H), 1.33 (s, 8H), 1.0–2.1 (m, 6H), 3.40 (t, J=6.0 Hz, 2H), 3.93 (s, 6H); MS m/e (rel. intensity) 323 (M+, 2.1), 321 (M+, 2.0), 292 (4.4), 290 (5.1), 239 (8.6), 237 (7.1), 221 (34), 219 (33), 69 (71), 55 (100).

1-(10'-bromo decanyl)-4-methyl-2,6,7-trioxabicyclo [2.2.2] octane (21). White solid (74% yield); m.p. 51°–53° C.; IR ν (KBr) 2940, 2900, 2850, 2830, 1455, 1390, 1055, 985, 955 cm$^{-1}$; NMR-60 δ (CDCl$_3$) 0.80 (s, 3H), 1.27 (s, 12H), 1.1–2.1 (m, 6H), 3.39 (t, J=6.0 Hz, 2H), 3.87 (s, 6H); MS m/e (rel. intensity) 350 (M+, 1.2), 348 (M+, 1.1), 321 (3.0), 319 (7.6), 269 (7.5), 248 (97), 144 (37), 55 (100).

1-(11'bromo undecananyl)-4-methyl-2,6,7-trioxabicyclo [2,2,29 octane (22). White solid (76%, yield); m.p. 47.5°, 48.5° C.; IR ν (KBr) 2900, 2835, 1460, 1045, 975 cm$^{-1}$; NMR-60 δ (CDCl$_3$) 0.79 (s, 3H), 1.25 (s, 14H), 1.1–2.1 (m, 6H), 3.37 (t, J=6.0 Hz, 2H), 3.85 (s, 6H); MS m/e (rel. intensity) 364 (M+, 3.5), 362 (M+, 3.4), 334 (13), 332 (13), 283 (15), 263 (85), 261 (97), 144 (51), 55 (100).

4. Preparation of 17α-alkynylamide estradiols (scheme 4B)

General Procedure for Coupling Reaction

In a flame-dried flask under argon atmosphere, 3,17β-bis tetrahydropyranyl ethinylestradiol 23 (1.5 mmol) synthesized from commercial ethynyl estradiol and dihydropyran was dissolved in dry THF (40 ml) and HMPA (6.0 mmol). The solution was cooled at −78° C. and n-BuLi (3.0 mmol) was added. After 2 h, appropriate bromo ortho ester 19-22 (6.0 mmol) in dry THF (10 ml) was added at −78° C. The mixture was allowed to return slowly at room temperature and keeped at this temperature overnight. Then, brine was added and the reaction mixture was extracted with ethylacetate. The organic phase was dried over MgSO$_4$ and the solvent was removed under reduced pressure. The crude product was purified by chromatography (hexane-ethylacetate-triethylamine/96:4:1 to 50:50:1, v/v/v) to give coupling product 24-27, unreacted steroid 23 (61, 22, 57%) and small quantity of undetermined product.

1-{3',17'β-bis [(tetrahydro-2"H-pyran-2"yl)oxy] estra-1',3',5'(10')-trien-17'α-yl}07-(4'-methyl-2',6',7'-trioxabicyclo [2'.2'.2'] octan-1'-yl)-1-heptyn (24). Colorless oil (15% yield); IR ν (neat) 2920, 2855, 2230 w, 1600, 1485 cm$^{-1}$; NMR-60 δ (CDCl$_3$) 0.75 (s, 3H), 0.88 (s, 3H), 2.80 (m, 2H), 3.2–4.1 (m, 4H), 3.80 (s, 6H), 4.9–5.3 (m, 1H), 5.34 (s, 1H), 6.75 (m, 2H), 7.19 (d, J=8.0 Hz, 1H); MS m/e (rel. intensity) 579 (M+-DHP, 4.0), 564 (1.1), 494 (12), 477 (12), 374 (13), 85 (100).

1-{3',17'β-bis [(tetrahydro-2"H-pyran-2"yl)oxy] estra-1',3',5'(10')-trien-17'α-yl}-10-(4'methyl-2'.6'.7'-trioxabicyclo [2'.2'.2'] octan-1'-yl)-1-decyne (25). Colorless oil (15%) yield); IR ν (neat) 2915, 2850, 2210 w, 1600, 1485 cm⁻¹; NMR-200 δ (CDCl₃) 0.79 (s, 3H), 0.90 (s, 3H), 2.24 (t, J=6.6 Hz, 2H), 2.83 (m, 2H), 3.55 (m, 2H), 3.89 (s, 6H), 3.95 (m, 2H), 4.98 and 5.19 (2s, 1H), 5.39 (s, 1H), 6.78 (d, J=2.6 Hz, 1H), 6.84 (dd, J₁=2.6 Hz and J₂=8.4 Hz, 1H), 7.22 (d, J=8.4 Hz, 1H); MS m/e (rel. intensity) 620 (M+-DHP, 4.8), 535 (13), 518 (8.9), 85 (100). 1-{3'17'β-bis [(tetrahydro-2"H-pyran-2"yl)oxy] estra-1',3',5'(10')-trien-17'α-yl}-12-(4'-methyl-2',6',7'-trioxabicyclo [2'.2'.2'] octan-1'-yl)-1-dodecyne (26). Colorless visquous oil (42% yield); IR ν (neat) 2920, 2850, 2210 vw, 1600, 1485 cm⁻¹; NMR-200 δ (CDCl₃) 0.79 (s, 3H), 0.90 (s, 3H), 2.25 (t, J=6.6 Hz, 2H), 2.83 (m, 2H), 3.55 (m, 2H), 3.89 (s, 6H), 3.95 (m, 2H), 5.0 and 5.2 (2s, 1H), 5.39 (s, 1H), 6.78 (d, J=2.6 Hz, 1H), 6.84 (dd, J₁=2.6 Hz and J₂=8.4 Hz, 1H), 7.21 (d, J=8.4 Hz, 1H); MS m/e (rel. intensity) 649 (M+-DHP, 6.1), 634 (0.7), 564 (22), 547(16), 85 (100).

1-(3'17'β-bis[(tetrahydro-2"H-pyran-2"-yl)oxy]estra-1'3'5'(10')-trien-1,17'α-yl}-13-(4'methyl-2',6',7'-trioxabicyclo[2'.2'.2']octan-1'yl)-1-tride cyne (27). Colorless visquous oil (35% yield); IR ν (neat) 2915, 2850, 2290 vw, 1600, 1490 cm⁻¹; NMR-200 δ (CDCl₃) 0.80 (s, 3H), 0.90 (0.3H), 2.25 (t, J=6.6 Hz, 2H), 2.83 (m, 2H), 3.53 (m, 2H), 3.89 (s, 6H), 3.95 (m, 2H), 5.0 and 5.2 (2s, 1H), 5.39 (s, 1H), 6.78 (d, J=2.2 Hz, 1H), 6.84 (dd, J₁=2.6 and J₂=8.4 Hz, 1H), 7.21 (d, J=8.4 Hz, 1H).

General Procedure for Ortho Ester and di-THP Hydrolysis

The product with ortho ester and di-THP group (0.22–0.63 mmol) was dissolved in MeOH (80–120 ml) and p-toluenesulfonic acid (0.17–0.23 mmol) was added. The solution was stirred at room temperature for 2–3 h. Then, water was added, MeOH was removed under reduced pressure and residue was extracted with ethylacetate. After evaporation of solvent, the crude product was purified by column chromatography (hexane-ethylacetate/5:5, v/v) to give ester compound with free hydroxyl group.

8-(3',17'β-dihydroxy estra-1',3',5'(10')-trien-17'α-yl)-7-octynoate ester of 2',2'-dihydroxymethyl propanol (28). Colorless visquous oil (70% yield); IR ν (film) 3340, 2910, 2850, 1710, 1600, 1485 cm⁻¹; NMR-200 δ (CDCl₃) 0.83 (s, 3H), 0.86 (s, 3H), 2.27 (t, J=6.4 Hz, 2H), 2.38 (t, J=7.1 Hz, 2H), 2.81 (m, 2H), 3.54 (s broad, 4H), 4.17 (s, 2H), 4.87 (s, 1H), 6.56 (d, J=2.6 Hz, 1H), 6.63 (dd, J₁=2.6 Hz and J₂=8.4 Hz, 1H), 7.17 (d, J=8.4 Hz, 1H); MS m/e (rel. intensity) 512 (M+, 14), 494 (97), 479 (17), 466 (11), 270 (48), 159 (100).

11-(3',17'β-dihydroxy estra-1',3',5'(10')-trien-17'α-yl)-10-undecynoacte ester of 2',2'-dihydroxymethyl propanol (29). Colorless visquous oil (61% yield); IR ν (neat) 3360, 2910, 2840, 2210 vw, 1710, 1600, 1485 cm⁻¹; NMR-200 (CDCl₃) δ 0.84 (s, 3H), 0.86 (s, 3H), 2.24 (t, J=7.0 Hz, 4H), 2.79 (m, 2H), 3.34 (s broad, 2H), 3.56 (s broad, 4H), 4.13 (s, 2H), 6.57 (s_app, 1H), 6.63 (dd, J₁=2.6 Hz and J₂=8.4 Hz, 1H), 7.14 (d, J=8.4 Hz, 1H) MS m/e (rel. intensity) 554 (M+, 5.0), 536 (57), 520 (10), 507 (7.6), 435 (14), 419 (20), 270 (39), 160 (85), 133 (100).

13-(3',17'β-dihydroxy estra-1',3',5'(10')-trien-17'α-yl)-12-tridecynoate ester of 2',2'-dihydroxymethyl propanol (30). Colorless visquous oil (78% yield); IR ν (film) 3360, 2915, 2840, 1710, 1600, 1490 cm⁻¹; NMR-200 δ (CDCl₃) 0.83 (s, 6H), 2.25 (m, 4H), 2.78 (m, 2H), 3.53 (s broad, 4H), 4.09 (s, 2H), 6.6 (m, 2H), 7.10 (d, J=8.0 Hz, 1H); MS m/e (rel. intensity) 582 (M+, 1.0), 563 938), 548 (5.7), 535 (3.5), 463 (5.7), 446 (13), 270 (44), 160 (57), 133 (58), 55 (100).

14-(3',17'β-dihydroxy estra-1',3',5'(10')-trien-17'α-yl)-13-tetradecynoate ester of 2',2'-dihydroxymethyl propanol (31). Colorless visquous oil (83% yield); IR ν (film) 3360, 2910, 2840, 2220 vw, 1710, 1605, 1490 cm⁻¹; NMR-200 δ (CDCl₃) 0.85 (s, 3H), 0.87 (s, 3H), 2.25 (t, J=6.6 Hz, 2H), 2.33 (t, J=7.1 Hz, 2H), 2.80 (m, 2H), 2.9 (m, 2H), 3.58 (s broad, 4H), 4.20 (s, 2H), 5.72 (s, 1H), 6.56 (d, J=2.6 Hz, 1H), 6.62 (dd, J₁=2.6 Hz and J₂=8.4 Hz, 1H), 7.15 (d, J=8.8 Hz, 1H).

General Procedure for Hydrolysis of Ester Following by Amide Formation

At a solution of ester (0.14–0.49 mmol) in MeOH (12–50 ml) was added aqueous solution of KOH 10% w/v (6–25 ml) and mixture was refluxed under argon atmosphere for 24 h. Thereafter, water was added and MeOH was evaporated under reduced pressure. The resulting solution was acidified with HCl and extracted with ethylacetate. Organic phase was washed with water, brine and dried over MgSO₄. Without purification, the crude carboxylic acid (IR acid band at 1700 and 2400–3600 cm⁻¹) was dissolve din dry CH₂Cl₂ (20–70 ml) and tributylamine (0.58–2.04 mmol). The mixture was cooled at −10° C., isobutyl chloroformate 0.68–2.41 mmol) was added and allowed to react 30 min. At this time, N-methybutylamine in excess (4.2–16.0 mmol) was added and the cooling bath was removed. After 2 h, CH₂Cl₂ was added and organic phase was washed with HCl (1N) and dried over MgSO₄. The solvent was removed and crude amide purified by column chromatography (hexane-ethylacetate/7:3, v/v).

N-butyl, N-methyl-8-[3'-(i-butyloxy carbonyloxy)-17'β-hydroxy estra-1',3',5'(10')-trien-17'α-yl]-7octynamide (32). Colorless oil (79% yield); IR ν (neat) 3380, 2920, 2850, 1745, 1620 cm⁻¹; NMR-200 δ (CDCl₃) 0.87 (s, 3H), 0.91 and 0.94 (2t, J=7.3 Hz, 3H), 1.00 (d, J=6.6 Hz, 6H), 2.85 (m, 2H), 2.89 and 2.91 (2s, 3H), 3.22 and 3.33 (2t, J=7.5 Hz, 2H), 4.02 (d, J=7.0 Hz, 2H), 6.88 (d, J=2.6 Hz, 1H), 6.93 (dd, J₁=2.6 Hz and J₂=8.4 Hz, 1H), 7.29 (d, J=8.4 Hz, 1H); MS m/e (rel. intensity) 579 (M+, 12), 561 (26), 546 (11), 461 (6.7), 447 (3.7), 270 (84), 57 (100), EMS M+ calculated for C₃₆H₅₃O₅N: 579.3923; found: 579.3970.

N-butyl, N-methyl-11-[3'-(i-butyloxy carbonyloxy)-17'β-hydroxy estra-1',3',5'(10')-trien-17'α-yl]-10-undecynamide (33). Colorless oil (67% yield); IR ν (neat) 3370, 2910, 2840, 1745, 1620 cm⁻¹; NMR-200 δ (CDCl₃) 0.87 (s, 3H), 0.92 and 0.95 (2t, J=6.6 Hz, 3H), 1.00 (d, J=7.0 Hz, 6H), 2.86 (m, 2H), 2.90 and 2.94 (2s, 3H), 3.24 and 3.35 (2t, J=7.3 Hz, 2H), 4.03 (d, J=6.6 Hz, 2H), 6.88 (d, J=2.6 Hz, 1H), 6.93 (dd, J₁=2.6 Hz and J₂=8.8 Hz, 1H), 7.30 (d, J=8.1 Hz, 1H); MS m/e (rel. intensity) 621 (M+, 2.1), 606 (2.4), 602 (6.2), 212 (43), 159 (69), 142 (68), 114 (100).

N-butyl, N-methyl-13-[3'(i-butyloxy carbonyloxy)-17'β-hydroxy estra-1',3',5'-(10')-trien-17'α-yl]-12-tridecynamide (34). Colorless oil (89% yield); IR ν (neat) 3370, 2920, 2840, 1745, 1620 cm⁻¹; NMR-200 δ (CDCl₃) 0.87 (s, 3H), 0.92 and 0.95 (2t, J=7.0 Hz, 3H), 1.00 (d, J=7.0 Hz, 6H), 2.86 (m, 2H), 2.90 and 2.96 (2s, 3H), 3.25 and 3.35 (2t, J=7.4 Hz, 2H), 4.02 (d, J=6.6 Hz, 2H), 6.88 (d, J=2.2 Hz, 1H), 6.93 (dd, $J_1$=2.6 Hz and $J_2$=8.4 Hz, 1H), 7.30 (d, J=8.8 Hz, 1H); MS m/e (rel intensity) 649 (M+, 20), 633 (15), 631 (18), 616 (8.2), 531 (15), 516 (5.6), 270 (85), 57 (100); EMS M+ calculated for $C_{41}H_{63}O_5N$: 649.4705; found: 649.4643.

N-butyl, N-methyl-14-[3'(i-butyloxy carbonyloxy)-17'β-hydroxy estra-1',3'5'(10')-trien-17'α-yl]-13-tetradecynamide (35). Colorless oil (83%, yield); IR ν (neat) 3380, 2910, 2840, 1750, 1625 cm$^{-1}$; NMR-200 δ (CDCl$_3$) 0.87 (s, 3H), 0.92 and 0.95 (2t, J=7.0 Hz, 3H), 1.00 (d, J=6.6 Hz, 6H), 2.85 (m, 2H), 2.91 and 2.96 (2s, 3H), 3.25 and 3.36 (2t, J =7.4 Hz, 2H), 4.03 (d, J=6.6 Hz, 2H), 6.88 (d, J=2.6 Hz, 1H), 6.93 (dd, $J_1$=2.9 Hz and $J_2$=8.4 Hz, 1H), 7.30 (d, J=8.8 Hz, 1H); MS m/e (rel. intensity) . . .

Hydrolysis of Carbonate

Hydrolysis of carbonate compounds 32–35 was performed as follows: carbonate derivatives were dissolved in methanol (10 ml) $K_2CO_3$ (1%; p/v) in aqueous methanol (25:75, v/v) (10 ml) was added and the resulting solution was stirred at room temperature for 3 h. Reaction mixture was acidified with HCl (1N) and MeOH was evaporated under vacuum. The residue was extracted with ethyl acetate and organic phase was dried, evaporated and purified by column chromatography (hexane-ethylacetate) 6.5:3.5, v/v).

N-butyl, N-methyl-8-[3', 17'β-dihydroxy estra-1',3',5'(10')-trien-17'α-yl]-7-octynamide ("EM 157"). Purified by column chromatography (hexane-ethylacetate/4:6, v/v). Amorphous white solid (88% yield); IR ν (film) 3280, 2910, 2840, 1610 cm$^{-1}$; NMR-200 δ (CDCl$_3$) 0.87 (s, 3H), 0.91 and 0.94 (2t, J=7.0 Hz, 3H), 2.80 (m, 2H), 2.90 and 2.92 (2s, 3H), 3.22 and 3.34 (2t, J=7.3 Hz, 3H), 5.22 (s, 1H), 6.57 (d, J=2.9 Hz, 1H), 6.64 (dd, $J_1$=2.6 Hz and $J_2$=8.4 Hz, 1H), 7.16 (d, J=8.4 Hz, 1H); MS m/e (rel. intensity) 479 (M+,11), 462 (18), 460 (38), 446 (18), 270 (30), 114 (56), 88 (67), 44 (100); EMS M+ calculated for $C_{31}H_{45}O_3N$: 479.3399; found: 479.3369.

N-butyl, N-methyl-11-[3',17'β-dihydroxy estra-1',3',5'-(10')-trien-17'α-yl]-10-undecynamide ("EM 183"). Purified by column chromatography (hexane-ethylacetate/4:6, v/v). Amorphous white solid (83% yield); IR ν (KBr) 3300, 2910, 2840, 1610 cm$^{-1}$; NMR-200 δ (CDCl$_3$) 0.87 (s, 3H), 0.93 and 0.95 (2t, J=7.0 Hz, 3H), 2.80 (m, 2H), 2.91 and 2.94 (2s, 3H), 3.23 and 3.35 (2t, J=7.3 Hz, 2H), 5.30 (s, 1H), 6.57 (d, J=2.6 Hz, 1H), 6.64 (dd, $J_1$=2.6 Hz and $J_2$=8.4 Hz, 1H), 7.16 (d, J=8.1 Hz, 1H); MS m/e (rel. intensity) 521 (M+, 4.4), 505 (10), 502 (26), 489 (7.7), 487 (8.7), 270 (20), 114 (55), 88 (42), 44 (10).

N-butyl, N-methyl-13-[3',17'β-dihydroxy estra-1',3',5'(10')-trien-17'α-yl]-12-tridecynamide ("EM 163"). Purified by column chromatography (hexane-ethylacetate/7:3, v/v). Amorphous white solid (98% yield); IR ν (film) 3300, 2910, 2840, 1610 cm$^{-1}$; NMR-200 δ (CDCl$_3$) 0.88 (s, 3H), 0.93 and 0.95 (2t, J=7.0 Hz, 3H), 2.80 (m, 2H), 2.93 and 2.97 (2s, 3H), 3.25 and 3.38 (2t, J=7.5 Hz, 2H), 6.61 (d, J=2.6 Hz, 1H), 6.69 (dd, $J_1$=2.6 Hz and $J_2$=8.6 Hz, 1H), 6.87 (s, 1H), 7.14 (d, J=8.1 Hz, 1H); MS m/e (rel. intensity) 549 (M+, 8.7), 532 (17), 530 (23), 516 (12), 270 (30), 114 (35), 88 (45), 44 (100); EMS M+ calculated for $C_{36}H_{55}O_3N$: 549.4182, found: 549.4271.

N-butyl, N-methyl-14-[3',17'β-dihydroxy estra-1',3',5'(10')-trien-17'α-yl]-13-tetradecynamide ("EM 196"). Purified by column chromatography (hexane-etyhylacetate/6:4, v/v). Amorphous white solid (93% yield); IR ν (film) 3280, 2915, 2840, 1615 cm$^{-1}$; NMR-200 δ (CDCl$_3$) 0.88 (s, 3H), 0.94 and 0.95 (2t, J=7.0 Hz, 3H), 2.80 (m, 2H), 2.95 and 2.98 (2s, 3H), 3.26 and 3.39 (2t, J=7.3 Hz, 2H), 6.61 (d, J=2.2 Hz, 1H), 6.70 (dd, $J_1$=2.6 Hz and $J_2$=8.4 Hz, 1H), 7.13 (m, 2H: aromatic and phenolic hydrogen).

SCHEME 4

A

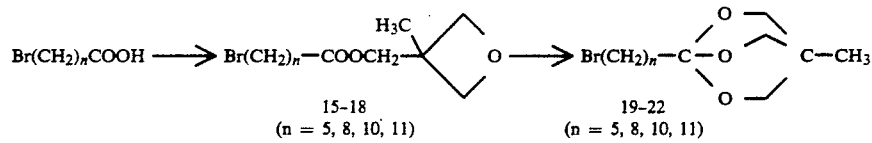

15-18
(n = 5, 8, 10, 11)

19-22
(n = 5, 8, 10, 11)

B

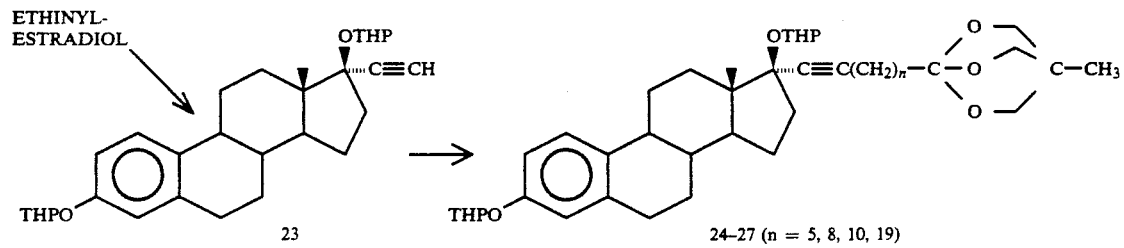

24-27 (n = 5, 8, 10, 19)

5,204,337
39    40
-continued
SCHEME 4
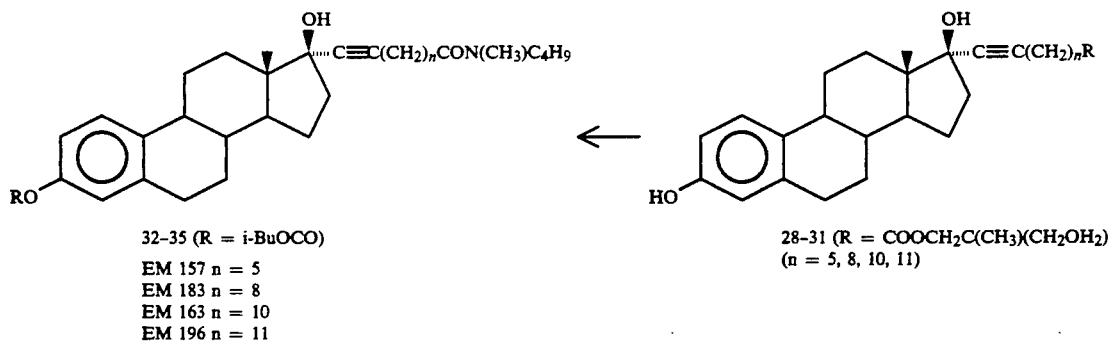
32-35 (R = i-BuOCO)
EM 157 n = 5
EM 183 n = 8
EM 163 n = 10
EM 196 n = 11
28-31 (R = COOCH$_2$C(CH$_3$)(CH$_2$OH$_2$)
(n = 5, 8, 10, 11)
20 ("EM 111") and its 17β-ethinyl derivatives ("EM 121").
EXAMPLE 6
N-n-butyl, N-methyl-(3'-17'β-dihydroxy-11'β-methoxy estra 1',3',5'(10')-trien 7'α-yl) undecanamide
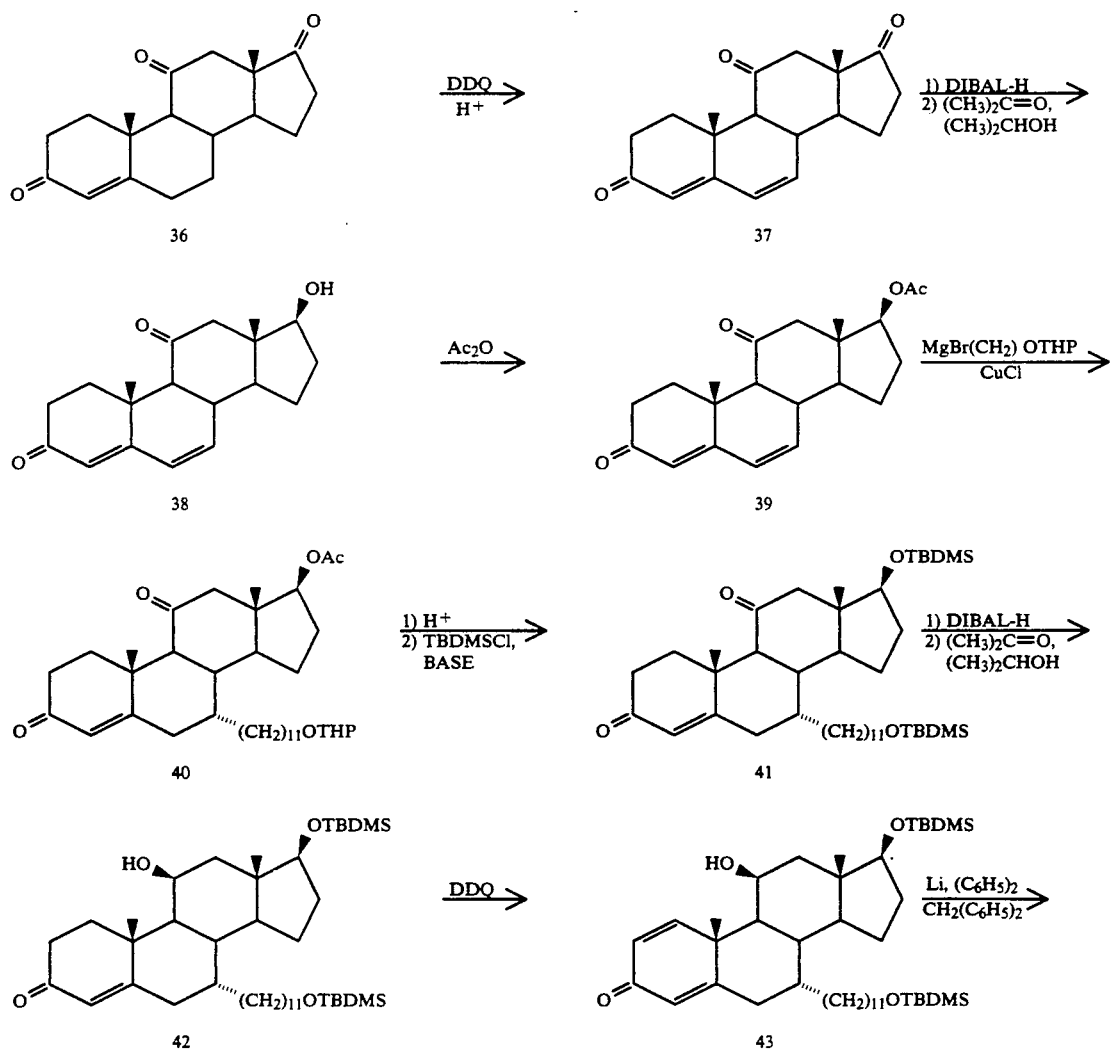

41 42
-continued
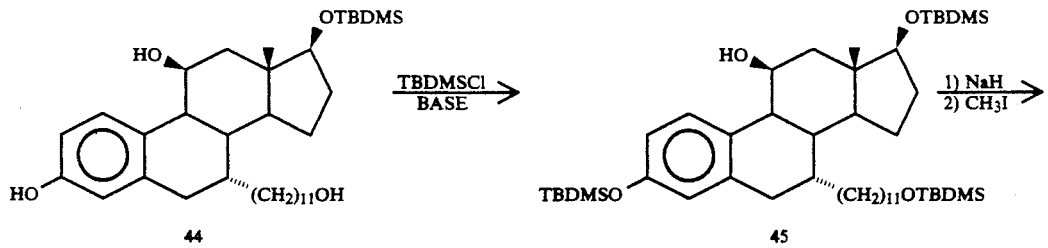
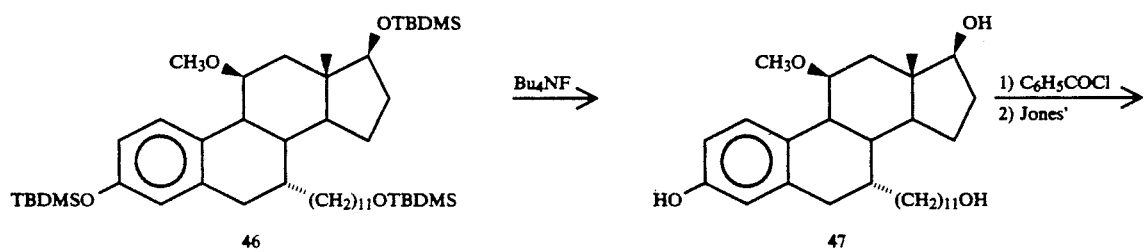
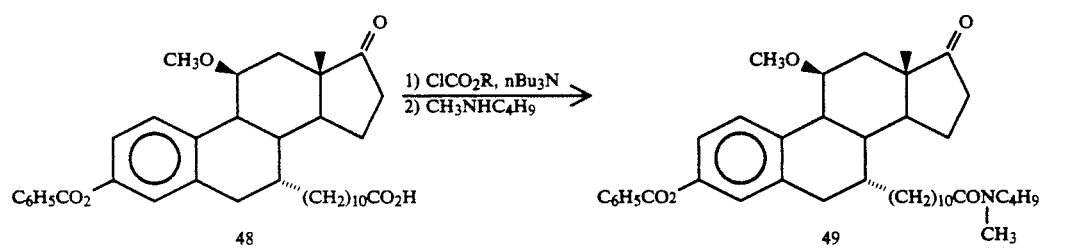
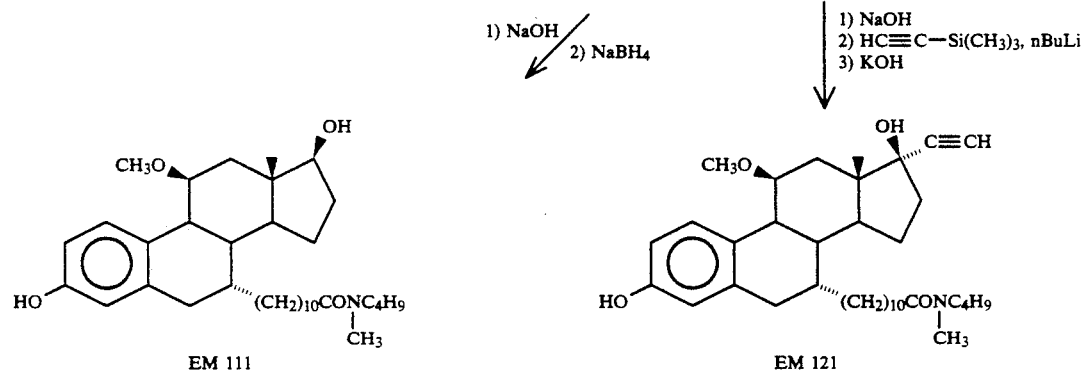
EM 111                                  EM 121
EXAMPLE 6 A
11β-chloromethyl derivatives
N-N-butyl, n-methyl, (11β-chloromethyl-3',17'β-dihydroxy-estra-1',3',5(10')-trien-7'α-yl) undecanamide (56), and its 17α-ethinyl derivatives (58).
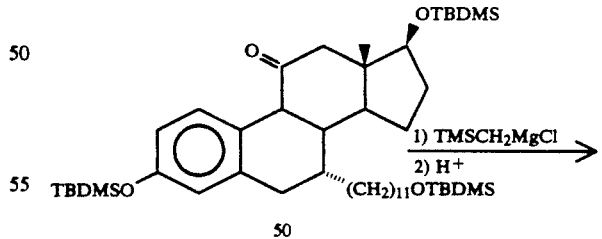
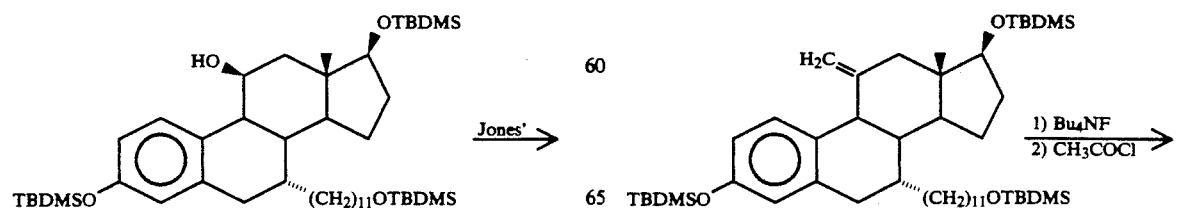

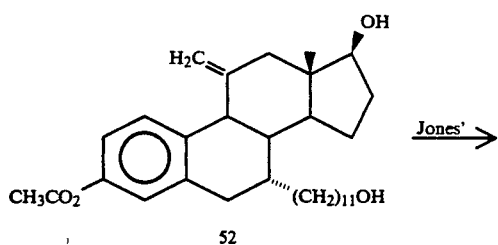
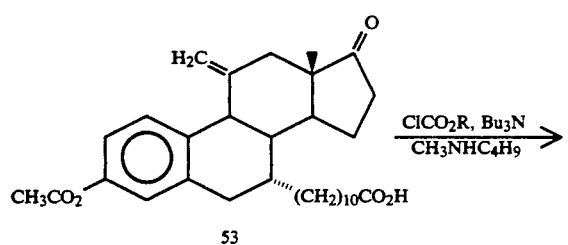
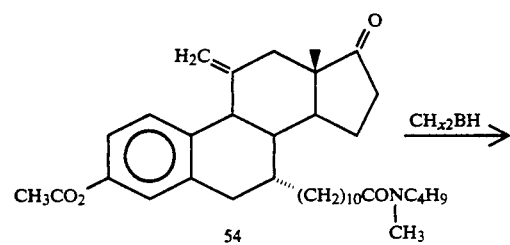
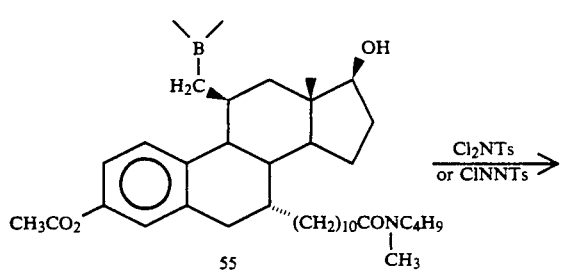
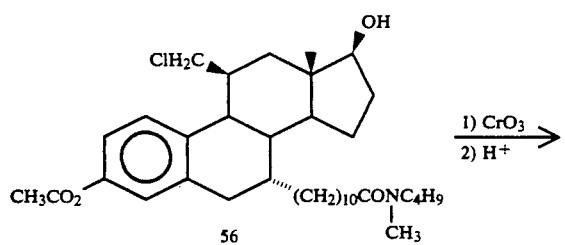
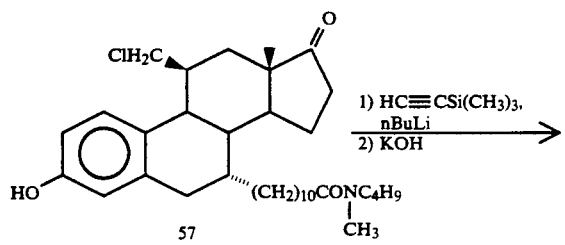
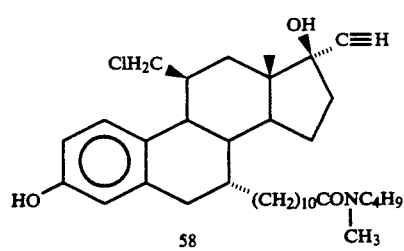
EXAMPLE 7
Compounds with aliphatic side-chain in 17α-position
N-n-butyl, n-methyl, 17′β-hydroxy-3′-methoxy estra-1′,3′,5′,(10′)-trien-17α′α-yl) undecanamide ("EM 103").

45

-continued

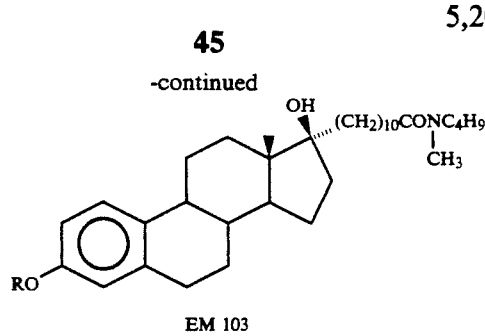

EM 103

EXAMPLE 8

17α-cyclopropyl derivatives

N-n-butyl, N-methyl-(17′α-cyclopropyl-3′,17β-dihydroxy estra-1′,3′,5′,(10)-trien-7′α-yl) undecanamide (68) and its 17′α-chlorocyclopropyl and 17′α-fluorocyclopropyl derivatives (69).

46

-continued

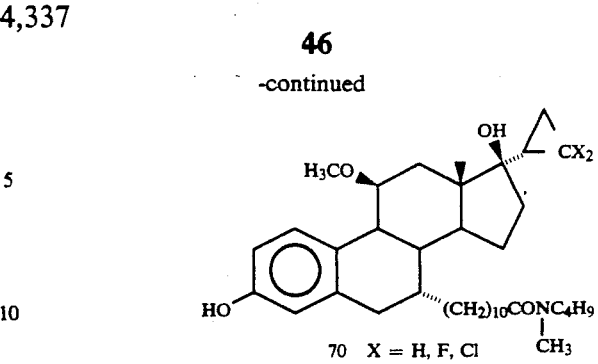

70   X = H, F, Cl

EXAMPLE 10

17α-cyanovinyl derivatives

N-n-butyl, N-methyl-(17′α-cyclopropyl-3′,17β-dihydroxy 11′β-methoxy estra 1′,3′,5′,(10)-trien-7′α-yl) undecanamide (73).

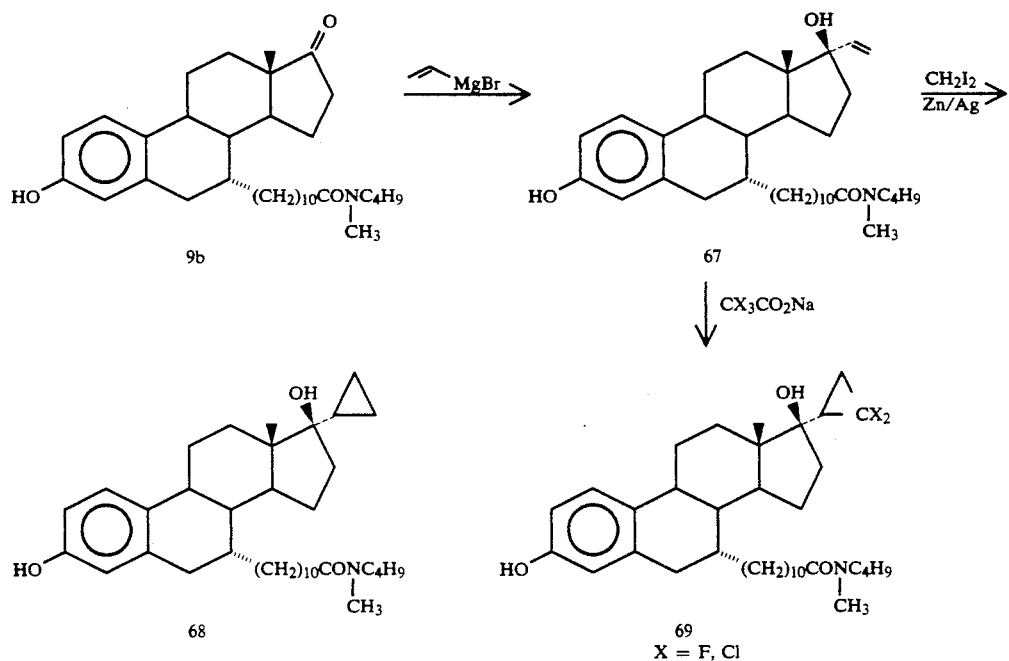

EXAMPLE 9

N-n-butyl, N-methyl-(17′α-cyclopropyl-3′,17β-dihydroxy 11′β-methoxy estra 1′,3′,5′,(10)-trien-7′α-yl) undecanamide (70 X=H) and its 17′α-chlorocylopropyl and 17′α-fluorocyclopropyl derivative (70, X=F, Cl).

Same example as Example 8 with compound 49 as starting material.

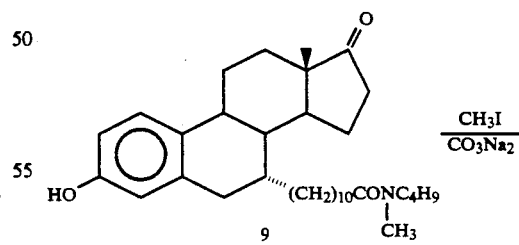

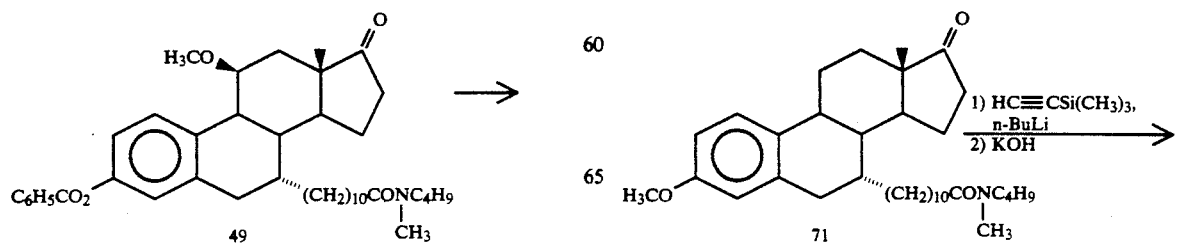

47
-continued
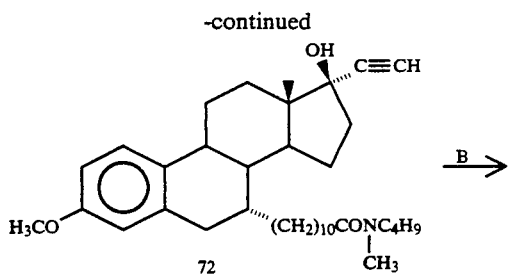
B →
B = 1) MeLi, CO₂
2) NH₃
3) NaBH₄—pyr
4) H₂, Lindlar cat.
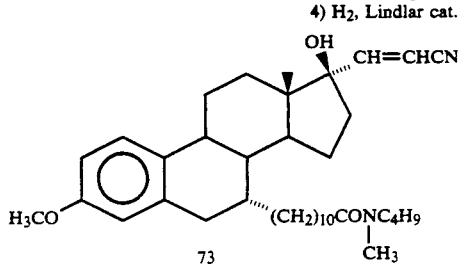
EXAMPLE 11
Compounds with aliphatic side chain in 15α-position
N-n-butyl, N-methyl-(3′,17β-dihydroxy 17′α-ethinyl estra 1′,3′,5′,(10)-trien-15′α-yl) undecanamide ("EM 108").
48
-continued
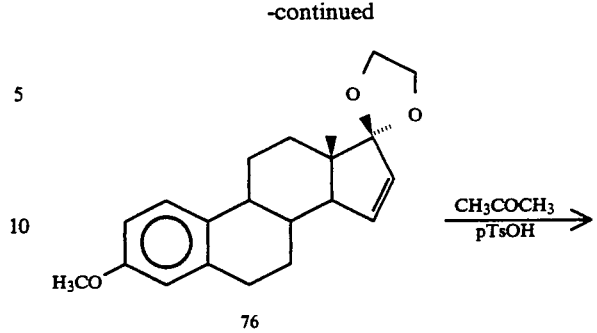
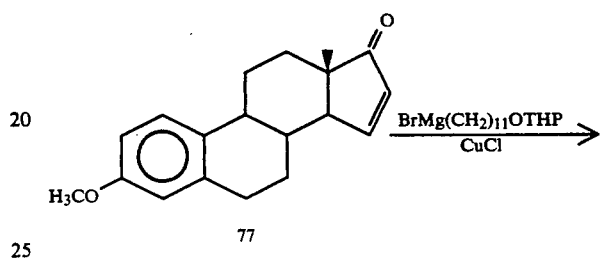
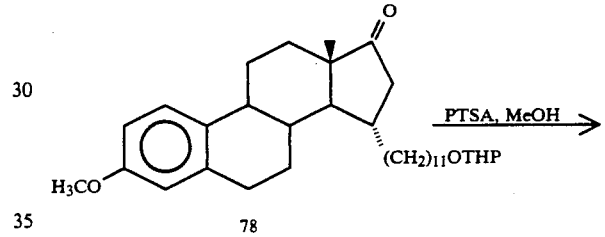
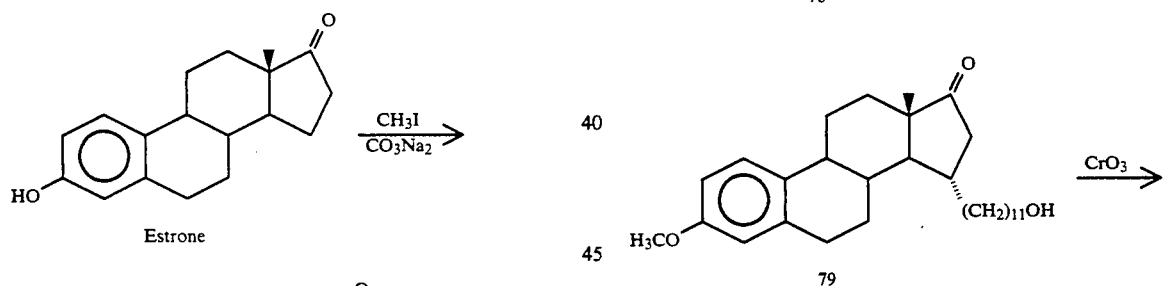
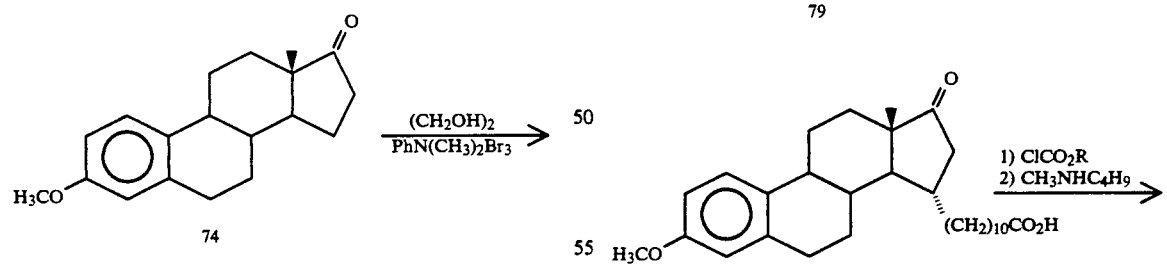
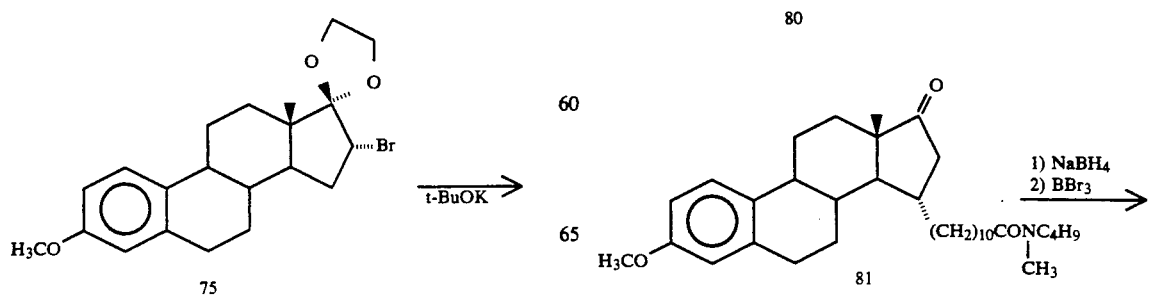

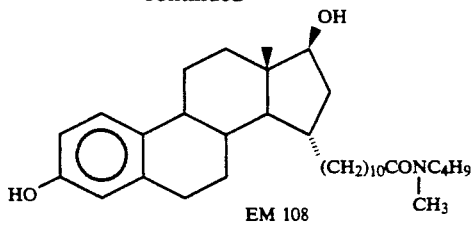 

EXAMPLE 12

17α-thioethyl derivatives

N-n-butyl, N-methyl-(3',17β-dihydroxy 17'α-thioethyl estra 1',3',5',(10)-trien-7'α-yl) undecanamide (82) and its ethyl disulfite derivative (83).

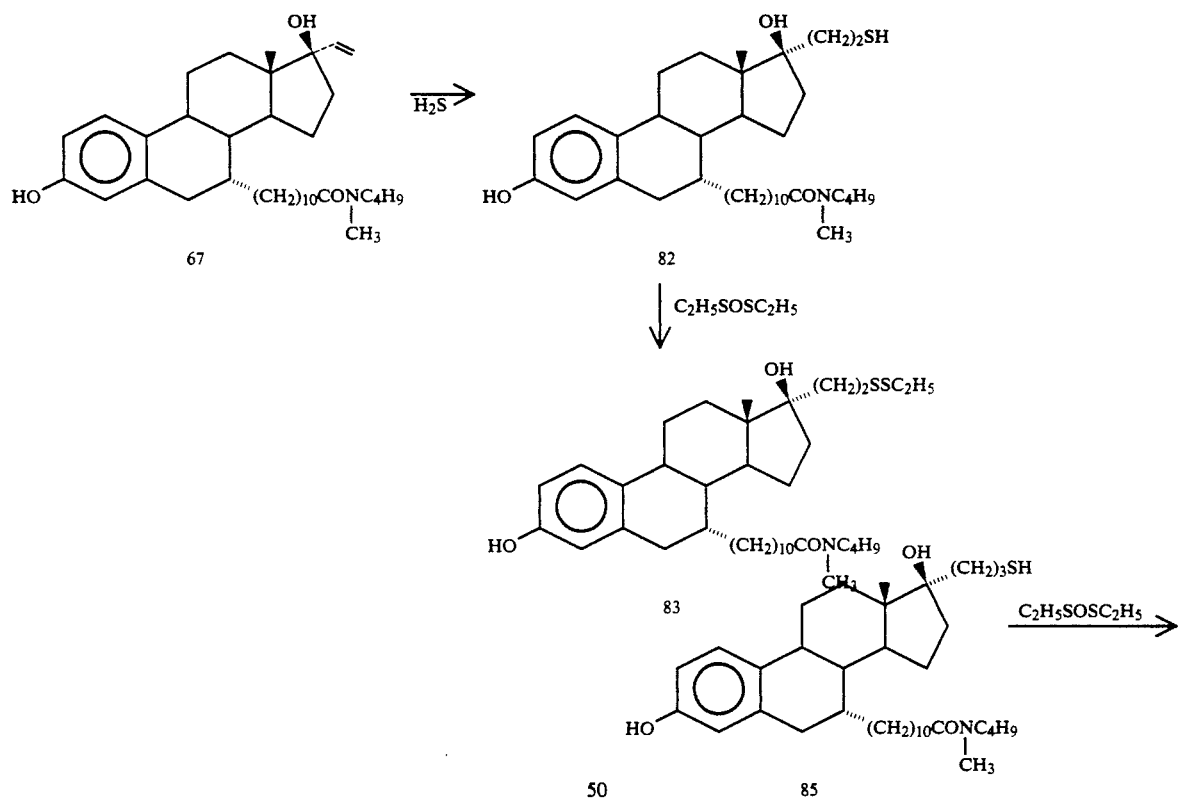

EXAMPLE 13

17α-thiopropyl derivatives

N-n-butyl, N-methyl-(3',17β-dihydroxy 17'α-thiopropyl estra-1',3',5'-derivatives (10')-trien-7'α-yl) undecanamide (84) and its ethyl disulfite derivative (86).

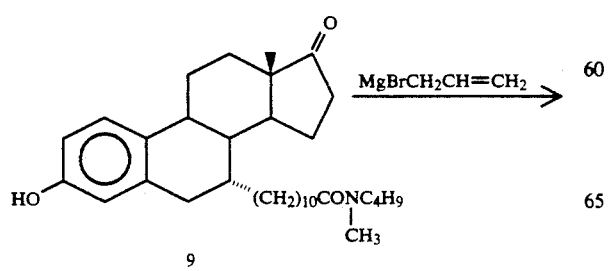

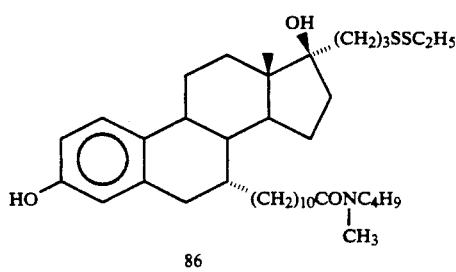

EXAMPLE 14

11β-ethyl derivatives

N-n-butyl, N-methyl-(3',17β-dihydroxy 17'α-ethinoyl-11β-ethyl estra 1',3',5'(10')trien-7'α-yl) undecanamide (97).

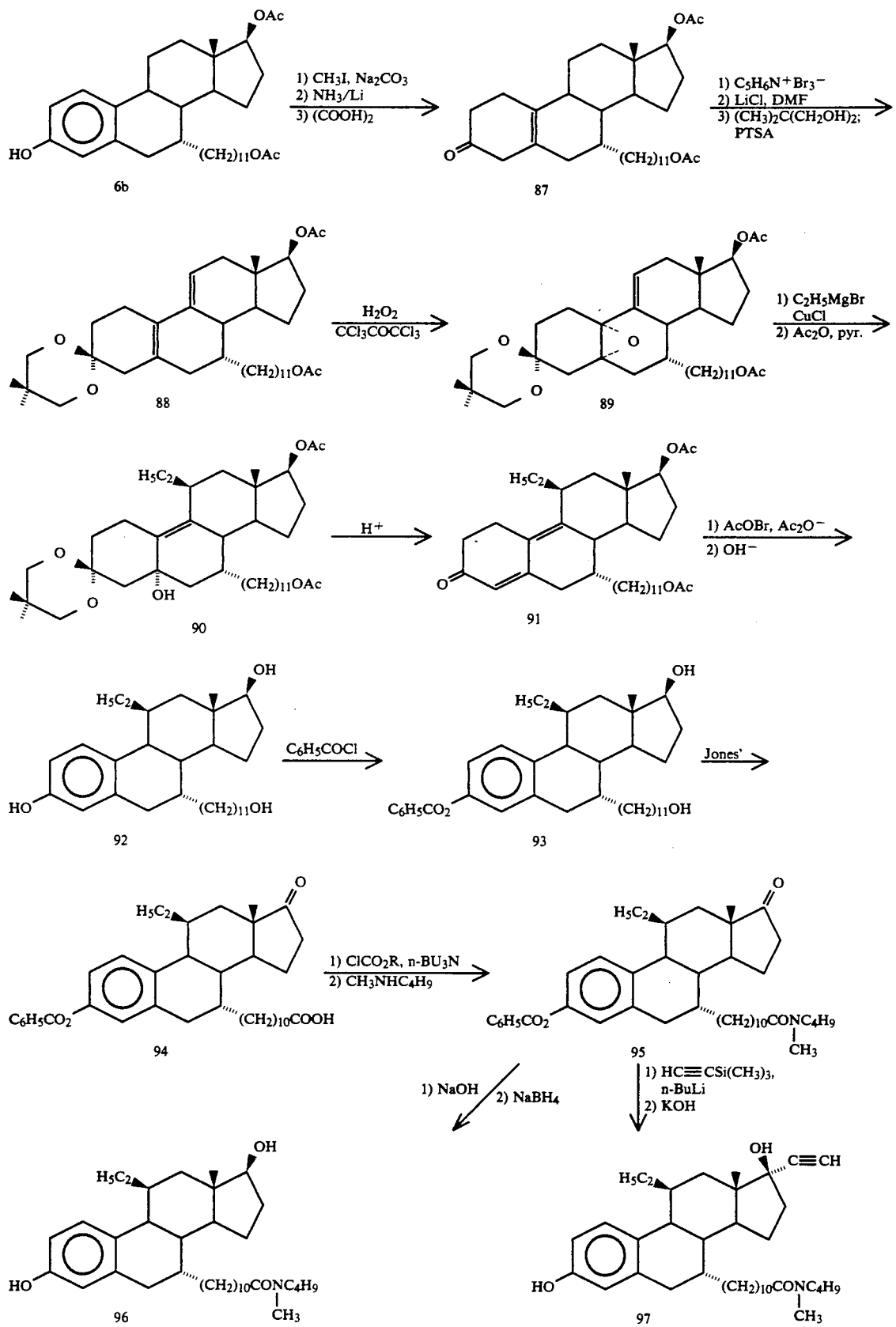

EXAMPLE 15
14,15 epoxide derivatives
N-n-butyl, N-methyl-3',17β-dibenzoyl-14',15'-epoxy-estra 1',3',5'(10')trien-7'α-yl) undecanamide ("EM 180") and ("EM 181").
EXAMPLE 16
N-n-butyl, N-methyl-11-(3',17'α-dihydroxy estra-1',3',5'(10')trien-7'α-yl) undecanamide ("EM 187")
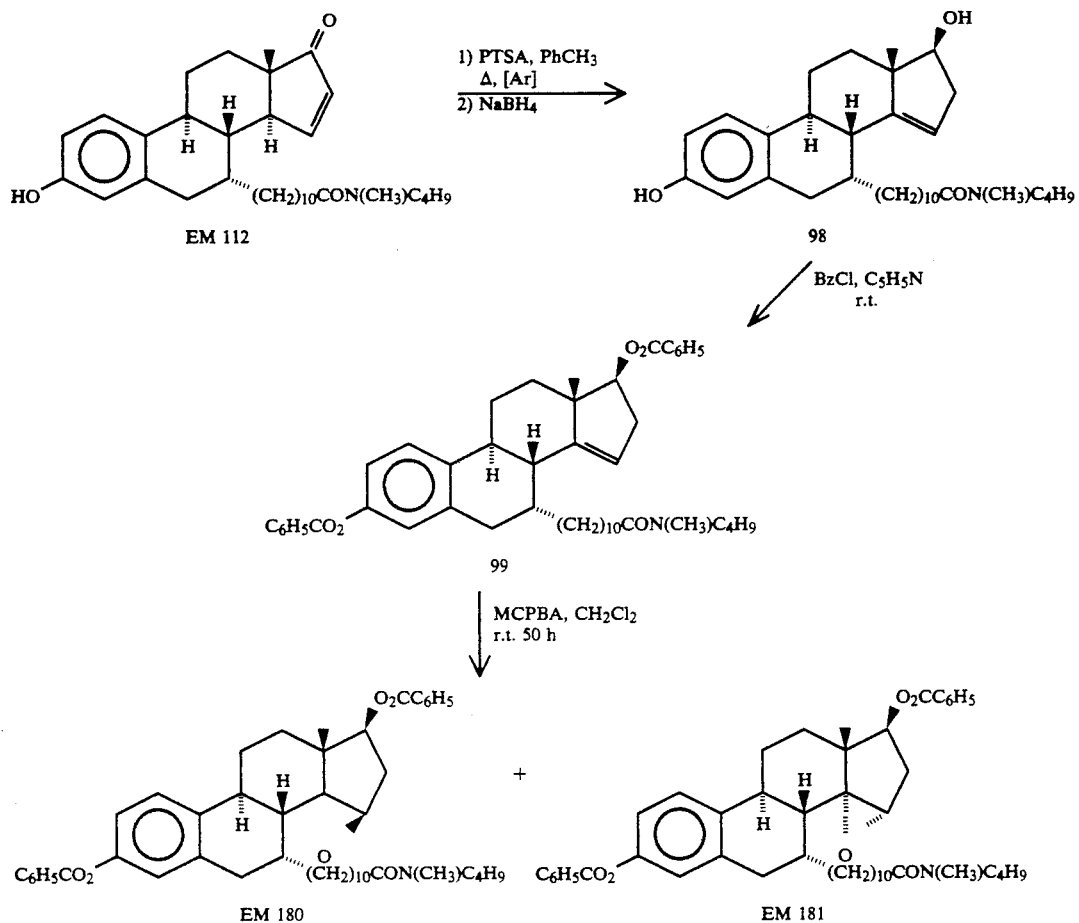
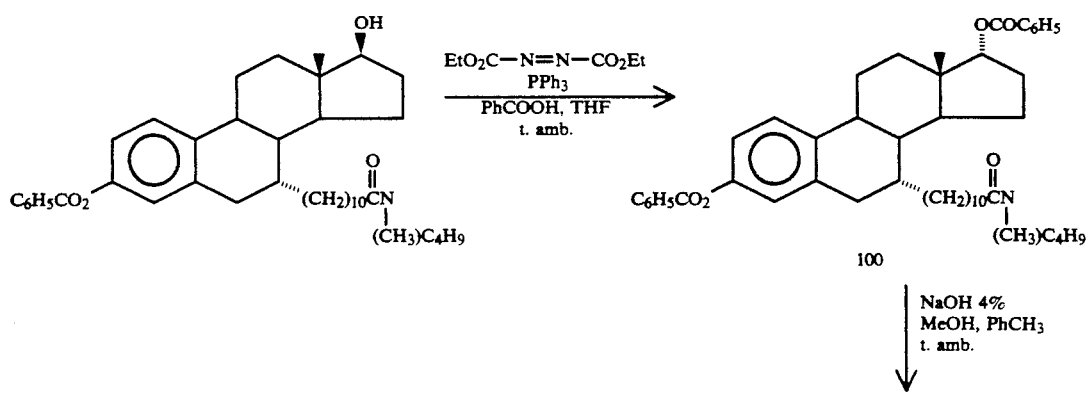

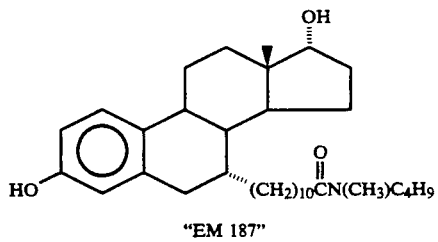
"EM 187"
EXAMPLE 17
N-n-butyl, N-methyl-11-(6'-hydroxy-2'-(4''-hydroxyphenyl)-3'-ethyl-indol-N'-yl) undecanamide (104).
The starting material 101 has been synthesized as described by Von Angerer et al., J. Med. Chem. 27: 1439–1447, 1984.
EXAMPLE 18
N-n-butyl, N-methyl-11-(6'-hydroxy-2'-(4''-hydroxyphenyl)-(1'2'-dehydronaphtalen-3'-yl) undecanamide (110).
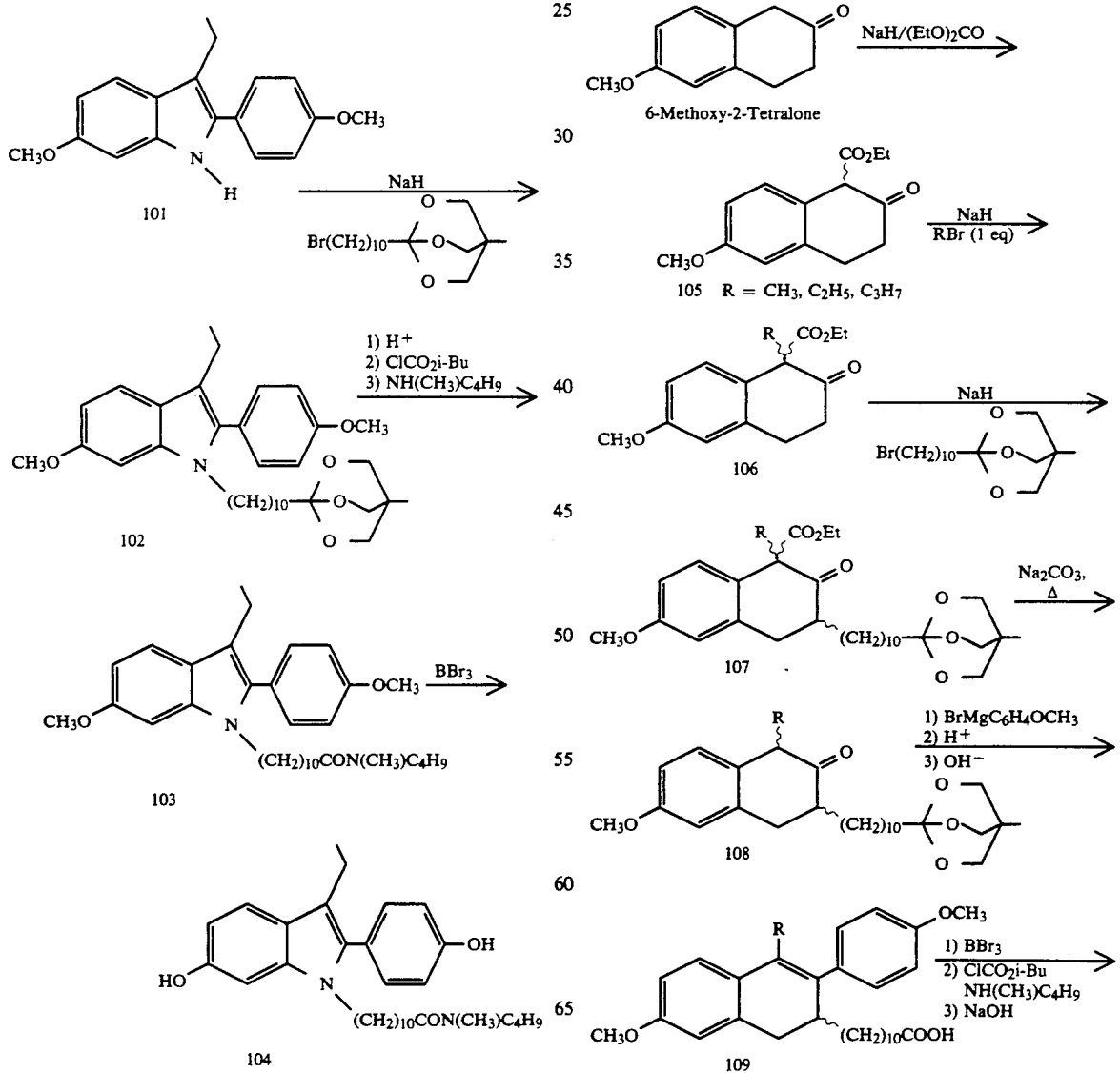

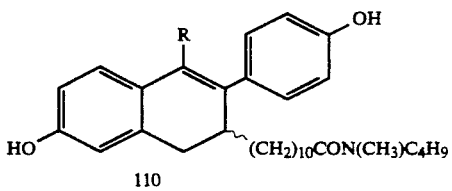
110

EXAMPLE 19

N-n-butyl, N-methyl-11-[4,4'-(1,2-diethyl-1,2-ethanydyl) bis-phenol-3-yl] undecanamide (115).

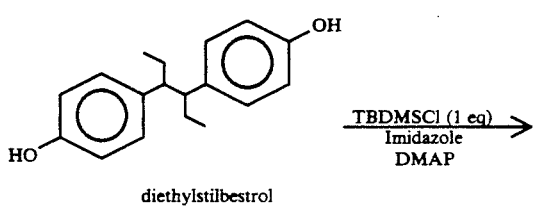
diethylstilbestrol

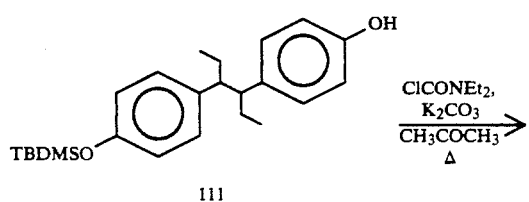
111

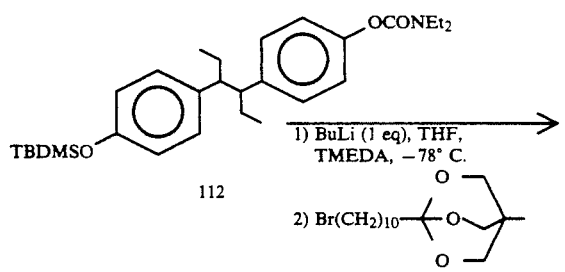
112

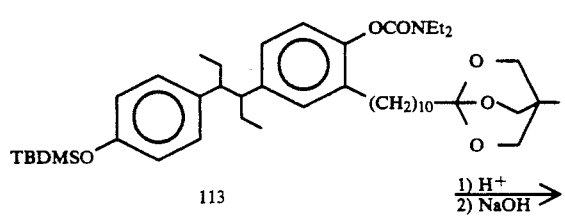
113

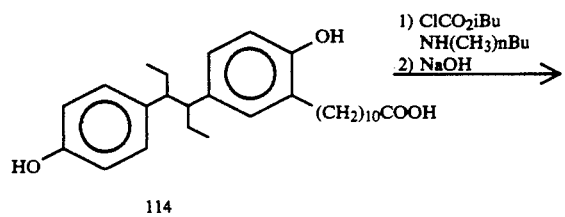
114

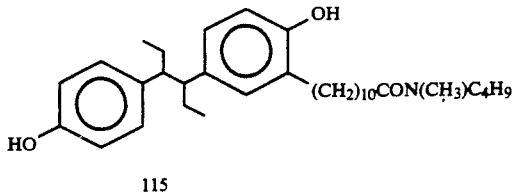
115

Other sex steroid activity inhibitors in accordance with the inventions may be synthesized by methods known in the art, by methods analogous to those set forth above and by modifying the synthesis set forth above in a manner known in the art.

The terms and descriptions used here are preferred embodiment set forth the way of illustration only and are not intended as limitations on the many variations which those of skill in the art will recognize to be possible in practicing the present invention as defined by the following claims.

What is claimed is:

1. A sex steroid activity inhibiting compound having, as part of its molecular structure, a substituted or unsubstituted estrogenic nucleus of the structure:

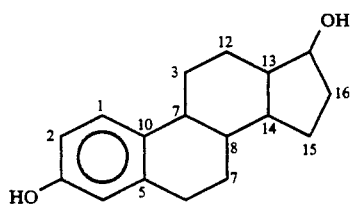

wherein said compound includes as another part of its molecular structure a 7α-N-n-butyl-N-methyl undecanamide side chain substitution; and wherein said estrogenic nucleus further includes at least one substitution selected from the group consisting of 15-chloro, 16-chloro, 15-iodo and 16-iodo.

2. A pharmaceutical composition comprising a pharmaceutically acceptable diluent or carrier and a therapeutically effective amount of a sex steroid activity inhibitor having, as part of its molecular structure, a substituted or unsubstituted estrogenic nucleus of the structure:

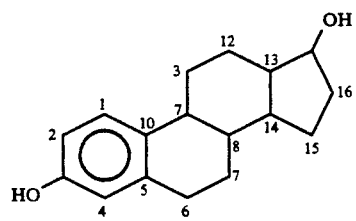

wherein said compound includes as another part of its molecular structure a 7α-N-n-butyl-methyl undecanamide side chain substitution; and wherein said nucleus further includes at least one substitution selected from the group consisting of 15-chloro, 16-chloro, 15-iodo and 16-iodo.

3. The pharmaceutical composition of claim 2 wherein said estrogenic nucleus includes a chloro-substitution in the 16 position.

4. A pharmaceutical composition comprising a pharmaceutically acceptable diluent or carrier and a therapeutically effective amount of at least one sex steroid inhibition selected from the group consisting of N-n-butyl-N-methyl-11-(16α-chloro-3',17'β-dihydroxy-estra-1',3',5'(10')-trien-7'α-yl) undecanamide ("EM 139")

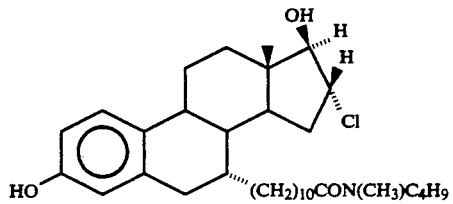

N-n-butyl-N-methyl-11-(16'α-chloro-3',17'α-dihydroxy-estra-1',4',5'(10')-trien-7'α-yl) undecanamide ("EM 170")

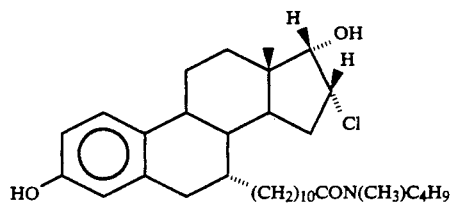

N-n-butyl-N-methyl-11-(16'α-iodo-3',17'β-dihydroxy-estra-1',3',5'(10')-trien-7'α-yl) undecanamide ("EM 156")

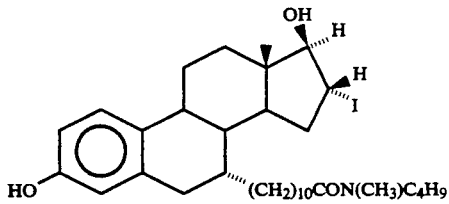

5. A method for inhibiting sex steroid activity comprising administering to a human or other warm-blooded animal, a pharmaceutically effective amount of the pharmaceutical composition of claim 2.

6. A method for inhibiting sex steroid activity comprising administering to a human or other warm-blooded animal, a pharmaceutically effective amount of the pharmaceutical composition of claim 4.

7. A method for treating an estrogen-related disease comprising administering to a patient afflicted with said disease, a pharmaceutically effective amount of the pharmaceutical composition of claim 2.

8. A method for treating an estrogen-related disease comprising administering to a patient afflicted with said disease, a pharmaceutically effective amount of the pharmaceutical composition of claim 4.

9. The pharmaceutical composition of claim 2, wherein said estrogenic nucleus further includes a 17α ethynyl substitution.

10. The compound of claim 1, wherein said estrogenic nucleus further includes a 17α ethynyl substitution.

* * * * *